United States Patent
Sung et al.

(10) Patent No.: US 11,850,288 B2
(45) Date of Patent: *Dec. 26, 2023

(54) GENE AND CELL THERAPY USING CELL FUSION TECHNOLOGY

(71) Applicant: CURAMYS INC., Seoul (KR)

(72) Inventors: Jung-Joon Sung, Seoul (KR); Seung-Yong Seong, Seoul (KR); Hee-Woo Lee, Seoul (KR); Ki Yoon Kim, Seoul (KR)

(73) Assignee: CURAMYS INC., Seoul (KR)

( * ) Notice: Subject to any disclaimer, the term of this patent is extended or adjusted under 35 U.S.C. 154(b) by 553 days.

This patent is subject to a terminal disclaimer.

(21) Appl. No.: 16/916,836

(22) Filed: Jun. 30, 2020

(65) Prior Publication Data
US 2020/0323997 A1    Oct. 15, 2020

Related U.S. Application Data

(63) Continuation of application No. 15/873,488, filed on Jan. 17, 2018, now Pat. No. 11,077,207, which is a continuation-in-part of application No. PCT/KR2016/007610, filed on Jul. 13, 2016.

(51) Int. Cl.
| | |
|---|---|
| *A61K 48/00* | (2006.01) |
| *C07K 14/005* | (2006.01) |
| *A61K 35/545* | (2015.01) |
| *C12N 5/0775* | (2010.01) |
| *C12N 5/12* | (2006.01) |
| *C12N 5/0793* | (2010.01) |
| *C12N 15/85* | (2006.01) |
| *A61P 21/00* | (2006.01) |
| *A61P 25/00* | (2006.01) |
| *A61K 35/30* | (2015.01) |
| *C12N 5/0735* | (2010.01) |
| *C12N 5/074* | (2010.01) |
| *C12N 5/16* | (2006.01) |
| *C12N 9/24* | (2006.01) |
| *A61K 38/00* | (2006.01) |

(52) U.S. Cl.
CPC .......... *A61K 48/005* (2013.01); *A61K 35/30* (2013.01); *A61K 35/545* (2013.01); *A61P 21/00* (2018.01); *A61P 25/00* (2018.01); *C07K 14/005* (2013.01); *C12N 5/0606* (2013.01); *C12N 5/0619* (2013.01); *C12N 5/0667* (2013.01); *C12N 5/0696* (2013.01); *C12N 5/12* (2013.01); *C12N 5/16* (2013.01); *C12N 9/2402* (2013.01); *C12N 15/85* (2013.01); *A61K 38/00* (2013.01); *C12N 2760/18822* (2013.01); *C12N 2760/18833* (2013.01)

(58) Field of Classification Search
CPC ........ A61K 48/005; A61P 21/00; A61P 25/00; C12N 5/0667; C12N 5/12
USPC ..................................................... 424/93.21
See application file for complete search history.

(56) References Cited

U.S. PATENT DOCUMENTS 5,486,359 A    1/1996   Caplan et al.

FOREIGN PATENT DOCUMENTS

| KR | 10-2007-0113088 A | 11/2007 |
| KR | 10-2008-0068098 A | 7/2008 |
| KR | 10-2008-0106152 A | 12/2008 |

OTHER PUBLICATIONS

Matsuura, 2013, The Cerebellum, 13:323-330.*
Deacon J. Vis. Exp. (75), e2609, doi:10.3791/2609 (2013).*
Hui Sun et al., "Therapeutic Potential of Mesenchymal Stromal Cells and MSC Conditioned Medium in Amyotrophic Lateral Sclerosis (ALS)-In Vitro Evidence from Primary Motor Neuron Cultures, NSC-34 Cells, Astrocytes and Microglia", PLOS ONE, Sep. 12, 2013, pp. 1-13.
Gussoni et al., "Dystrophin expression in the mdx mouse restored by stem cell transplantation", Magazines, Sep. 23, 1999, pp. 390-394, vol. 401.
Wang et al., "State-of-the-Art Human Gene Therapy: Part I. Gene Delivery Technologies", HHS Public Access, 2014, pp. 67-77, vol. 18 (97).
Bittner et al., "Recruitment of bone-marrow-derived cells by skeletal and cardiac muscle in adult dystrophic mdx mice", Article, pp. 391-396.
Bossart et al., "Paramyxovirus Entry", Database, pp. 1-34.
Ferrari et al., "Muscle Regeneration by Bone Marrow-Derived Myogenic Progenitors", Article, Mar. 6, 1998, pp. 1528-1530, vol. 279.
Long et al., "Targeted Cell Fusion Facilitates Stable Heterokaryon Generation In Vitro and In Vivo", PLOS ONE, Oct. 24, 2011, pp. 1-9, vol. 6 (10).
Lee, Hee-Woo et al.: "G-75:" Enhanced Fusion Ability of Hemagglutinin Neuraminidase/fusion-expressing Human Adipose Tissue-derived Mesenchymal Stem Cells with Motor Neurons, KSBMB International Conference 2015, May 12, 2015 (May 12, 2015), COEX, Seoul, Korea.
Silani, Vincenzo et al.: "Stem-Cell Therapy for Amyotrophic Lateral Sclerosis", The Lancet, Jul. 10, 2004 (Jul. 10, 2004), pp. 200-202, vol. 364, No. 9429.

(Continued)

*Primary Examiner* — Valarie E Bertoglio
(74) *Attorney, Agent, or Firm* — NKL LAW; Jae Youn Kim

(57) ABSTRACT

A gene and cell therapy using a cell fusion technology is proposed. Cells overexpressing hemagglutinin neuraminidase (HN) and fusion (F) proteins have effects of enhancing cell fusion with other cells, restoring cell damage through the cell fusion with damaged cells, and transferring a normal gene. Therefore, when a vector including genes encoding the HN and F proteins of the present invention or a cell transformed with the vector is clinically applied to neurodegenerative diseases, muscular diseases, and the like, an effect of reducing the damage of damaged cells through cell fusion can be expected.

7 Claims, 17 Drawing Sheets

Specification includes a Sequence Listing.

(56) References Cited

OTHER PUBLICATIONS

Kim, Jung Seok et al.: "Sendai F/ HN Viroplexes for Efficient Transfection of Leukemic T Cells", Yonsei Med. J., Sep. 2013 (Sep. 1, 2013), pp. 1149-1157, vol. 54, No. 5.

David Diaz et al., "Mild Cerebellar Neurodegeneration of Aged Heterozygous PCD Mice Increases Cell Fusion of Purkinje and Bone Marrow-Derived Cells", Cell Transplantation, 2012, p. 1595-1602, vol. 21.

Wei-Jian Yang et al., "Cell fusion contributes to the rescue of apoptotic cardiomyocytes by bone marrow cells", J. Cell. Mol. Med., Nov. 12, 2012, p. 3085-3095, vol. 16 No. 12.

Debra M. Eckert et al., "Mechanisms of Viralmembrane Fusion and Its Inhibition", Annu. Rev. Biochem., 2001, p. 777-810.

Amir Sapir et al., "Viral and Developmental Cell Fusion Mechanisms: Conservation and Divergence", Dev Cell., Jan. 2008, p. 11-21, vol. 14.

Nicholas A. Kouris et al., "Directed Fusion ofMesenchymal Stem Cells with Cardiomyocytes via VSV-G Facilitates Stem Cell Programming", Hindawi Publishing Corporation, 2012, p. 1-13, vol. 2012, Article ID 414038.

Doan, Steroids, 2015, 97:2-7.

Lovejoy, 2006, Molecular and Cellular Biology, 26:7977-7990.

Damjanov, 2009, Pathology Secrets, Chapter 1, Cell Pathology, pp. 7-18.

Manuel Alvarez-Dolado, Cell fusion: biological perspectives and potential for regenerative medicine, Frontiers in Bioscience, Feb. 2007, p. 1-12.

Yong Cang et al., Deletion of DDB1 in Mouse Brain and Lens Leads to p53-Dependent Elimination of Proliferating Cells, Cell, Nov. 30, 2006.

* cited by examiner

-1000
|
GAGTCAAGTCGAGTGCCAGCTGGGGAGGTACAAATCATCTTCAGTTCCACCTGGTTCAAACCTAGCTACACT
GATCTCTGCCTCATTTGTAAAATAGGGAGTTAGCTCTCCTCCTCCGGCATTCTGGAGATGCTTCAGGACTAGG
CTTCTGCTGCTCCTCCTTTGGGGTTGGGGACATGGAGGCTGTCTGATGAAGCCTGGGACCTGCATCTGCGGG
GCTGATTGCACTAGTCACCTGGGTGTTTAGGCTCTTCCTGTGAAATTCCTGCGTTGTATTTGAGCTTAGAATTT
GTATCGCAGTAGAGGCACTAATAGTGCTATCAAGTAATTTAGTGGAGAGTCCTTTCGTTTCTGGAGAAATTAA
AAGAGGTGAGCAAACACACCCCAGGTGATGTGTGAGGCTGGGATGATTGTTCTAAAGTCAGTTGAGGGCAT
TCGAGGGATCAGGAGGAGCTCGAAGAATTAAGCAAAGGAAAGCACGATTCTACTCTGGGATGTGCACAGAT
GGTCACCTCTTATCCCCAGTCTAGTCCTCCGCAGCCCTTCCTGTTTTAAAAGAGGGAAAACCCCGAGGACGC
CTGGAGCTATGGAGGAAGGAAGGAGGCAGAATCTGAGGAAGGGGCGCGGATCTGGGCTGGGAAGCCAGCA
GGCGGCCACTTAGGGCGTAGCAGACCAAAGAGGAGGCCAGTTCTGCCTGCGTACCGGTACTCTCGCTCTCA
TCCGGGTACTGCGACCTCTGGCGGTTAGGAGAAGGCGGGACCTCAGGGGGCGGGGCCTCGCTTGGTTGGCC
GCCTCGGGCTCCGTAAGTCCTCCAAGAGGCCAGGTGAGGCCGTCCCGTGATCCTCTGCGCCTGGCCTCTCTG
GCCTGCAACGTGTCTCAGGGGCGGAGGCAGCAGCCACGGAGTTGGCTGCGTGAGGGTGGGGGTTCTCAGTC
TCTTCGCTCGCGCCCGTCTCTCTATCGTCGCTCTAGGCGCCCCACGGGCCAACCCAAGGCCTCAATATG(Met)

FIG. 14

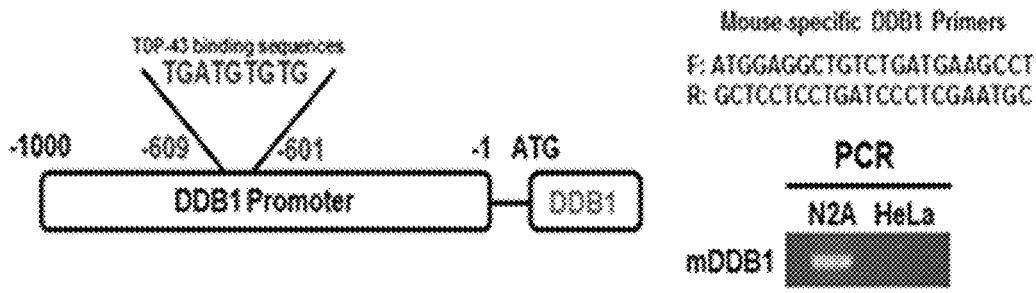

FIG. 15

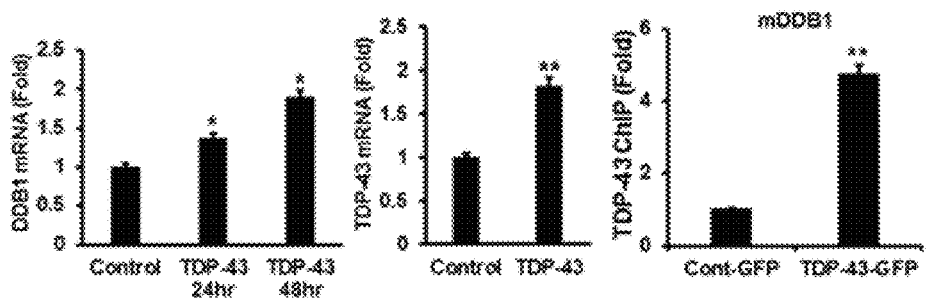

FIG. 16

- Intra-spinal cord injection

GENE AND CELL THERAPY USING CELL FUSION TECHNOLOGY

CROSS-REFERENCE TO RELATED APPLICATIONS

This application is a continuation of U.S. application Ser. No. 15/873,488 filed Jan. 17, 2018, which is a national stage application of PCT/KR2016/008444 filed Aug. 1, 2016, which claims priority to KR 10-2015-0101577, filed Jul. 17, 2015, the entire disclosure of which is incorporated herein by reference.

REFERENCE TO AN ELECTRONIC SEQUENCE LISTING

The contents of the electronic sequence listing (8-PK0172383CON-SequenceListing.txt; Size: 4,059 bytes; and Date of Creation: Mar. 27, 2018) is herein incorporated by reference in its entirety.

BACKGROUND OF THE INVENTION

Field of the Invention

The present invention relates to gene and cell therapy using a cell fusion technology, and more particularly, to gene and cell therapeutic agents using a cell fusion technology capable of enhancing cell fusion with other cells by transducing hemagglutinin neuraminidase (HN) and fusion (F) genes into cells and overexpressing the transduced cells and restoring cell damage through cell fusion with damaged or dying cells or cells having gene abnormality.

Description of the Related Art

Generally, diseases and aging are progressed by cell damage and apoptosis. The common diseases that cause the cell damage and the apoptosis include neurodegenerative diseases, myopathy, and the like.

With the rapid increase in the elderly population, neurodegenerative diseases including damages of the brain, the spine and the peripheral nerves have been continuously increased. The causes of the neurodegenerative diseases are not clear yet. In addition, a pathological mechanism of each neurodegenerative disease is known to act a little different mechanism. However, common causes include abnormal protein aggregation, dysfunction of mitochondria, abnormality of intracellular trafficking, oxygen radical injury, excitatory toxicity, autophagy/proteosomal dysfunction, neuroinflammation, deficiency of neurotrophic factors, abnormality of RNA metabolism, and the like. Since these various pathological mechanisms act, it is difficult to treat diseases by a therapeutic agent acting on any one mechanism, and thus, almost all clinical trials have so far failed. Therefore, a therapeutic agent that acts on a wider mechanism and has a powerful effect is required. These neurodegenerative diseases include Alzheimer's disease, Parkinson's disease, amyotrophic lateral sclerosis (ALS, Lou Gehrig's disease) which has a rapid progressing speed of the disease and the most serious severity of the aftereffect, and the like. Particularly, the ALS-related therapeutic agents are almost not existent except for riruzole and edaravone which are approved by the FDA in US and have only an effect of the prolonged survival for about 3 months or slightly slowing deterioration of the physical function respectively, and thus, the development of a therapeutic technology is urgent.

Other neurodegenerative diseases also have no therapeutic agent for a complete cure, and may be diseases in which a new therapeutic method including a stem cell therapy is desperately required.

Currently, various therapeutic methods, such as cell transplantation and the administration of drugs to improve the symptoms, are proposed to treat the neurodegenerative diseases, and especially recently, there is attention on cell therapy. However, a conventional cell therapy technology aims to insert health cells (alternatively, stem cells) into a diseased region to replace dead cells or improve an ambient environment of the dying cells to regenerate the dying cells, but the attempt has no effect or a slight effect in many preclinical or clinical trials. Further, in the case of neuronal cells, it is very important to form a neural circuit in terms of a function unlike other organs, and thus, it is very difficult for the cell supplied from the outside to be differentiated into the neuronal cells to restore the existing neural circuit as it is. Accordingly, in addition to the conventional methods, it is urgent to develop a new therapeutic method for reducing or protecting neuronal cell damage.

Meanwhile, as diseases causing cell damage, Duchenn muscular dystrophy (DMD) and Backer muscular dystrophy (BMD) are included in muscular diseases, and these diseases are caused by abnormality of a dystrophin gene existing in an X chromosome and about ⅓ thereof is caused by natural mutation and the rest is caused by sex-linkage. Both the DMD and the BMD are caused by the abnormality of the same gene, but the DMD is called a case in which a phenotype is severe due to frame-shift mutation and the like. In the case of the DMD, since the course of the disease is poor, in 9 to 13 years of age, almost all patients are unable to walk and may be accompanied by cognitive decline as well as weakness of muscles accompanied by cardiomyopathy and respiratory distress to lead to death.

In the case of the DMD, recently, a method of attempting treatment by exon skipping has emerged. Since the exon skipping targets a splicing enhancer sequence of exon 51 of a dystrophin gene and has a principle that restores only a reading frame converting the severe mutation to a less severe gene mutant, the exon skipping may not be a complete treatment alternative and is not a treatment method for targeting all DMDs.

Therefore, the present inventors made efforts to develop a therapeutic agent for cell damage-related diseases including neurodegenerative diseases, muscular diseases, and the like, and as a result, found that cells overexpressing hemagglutinin neuraminidase (HN) and fusion (F) proteins have enhanced cell fusion with other cells by the HN and F proteins and high ability of restoring cell damage in the dying cells, and normal dystrophin was expressed by cell fusion. In addition, the present inventors found that the present invention can be usefully used to restore the cell damage in diseases causing the cell damage such as neurodegenerative diseases and muscular diseases and introduce a normal gene, and then completed the present invention.

SUMMARY OF THE INVENTION

An object of the present invention is to provide a method for reducing cell damage including: administering a vector including genes encoding hemagglutinin neuraminidase (HN) and fusion (F) proteins or a cell transformed with the vector to a subject with a therapeutically effective dose.

Another object of the present invention is to provide a therapeutic agent and a therapeutic method for cell damage-related diseases including neurodegenerative diseases, muscular diseases, and the like using hemagglutinin neuraminidase (HN) and fusion (F) genes.

An exemplary embodiment of the present invention provides a method for reducing cell damage including: administering a vector including genes encoding hemagglutinin neuraminidase (HN) and fusion (F) proteins or a cell transformed with the vector to a subject with a therapeutically effective dose.

Another exemplary embodiment of the present invention provides a method for treating neurodegenerative diseases or neurological diseases including: administering a vector including genes encoding hemagglutinin neuraminidase (HN) and fusion (F) proteins or a cell transformed with the vector to a subject with a therapeutically effective dose.

Yet another exemplary embodiment of the present invention provides a method for treating degenerative muscular diseases or muscular diseases including: administering a vector including genes encoding hemagglutinin neuraminidase (HN) and fusion (F) proteins or a cell transformed with the vector to a subject with a therapeutically effective dose.

According to the present invention, since the cells overexpressing the hemagglutinin neuraminidase (HN) and fusion (F) proteins have excellent cell fusion ability with other cells by the HN and F proteins and ability of restoring cell damage in dying cells and transferring normal genes, the present invention can be used to reduce cell damage and introduce normal genes in diseases having cell damage and gene abnormality, such as neurodegenerative diseases and muscular diseases.

BRIEF DESCRIPTION OF THE DRAWINGS

The above and other aspects, features and other advantages of the present invention will be more clearly understood from the following detailed description taken in conjunction with the accompanying drawings, in which:

FIG. 14 illustrates confirming a TDP-43 binding motif which is a transcriptional factor (TF) in a promoter region of a gene DDB1 related with cell repair selected according to the exemplary embodiment of the present invention;

FIG. 15 illustrates a mouse DDB1 (mDDB1) promoter having TDP-43 binding sequences and a schematic diagram for preparing mDDB1 specific primers according to the exemplary embodiment of the present invention;

FIG. 16 illustrates an analysis of mDDB1 expression by TDP-43 in fused cells of a HeLa cell line transduced with GFP-TDP-43 and the N2A neuroblastoma cell line according to the exemplary embodiment of the present invention;

DETAILED DESCRIPTION OF THE PREFERRED EMBODIMENT

Figure 1:
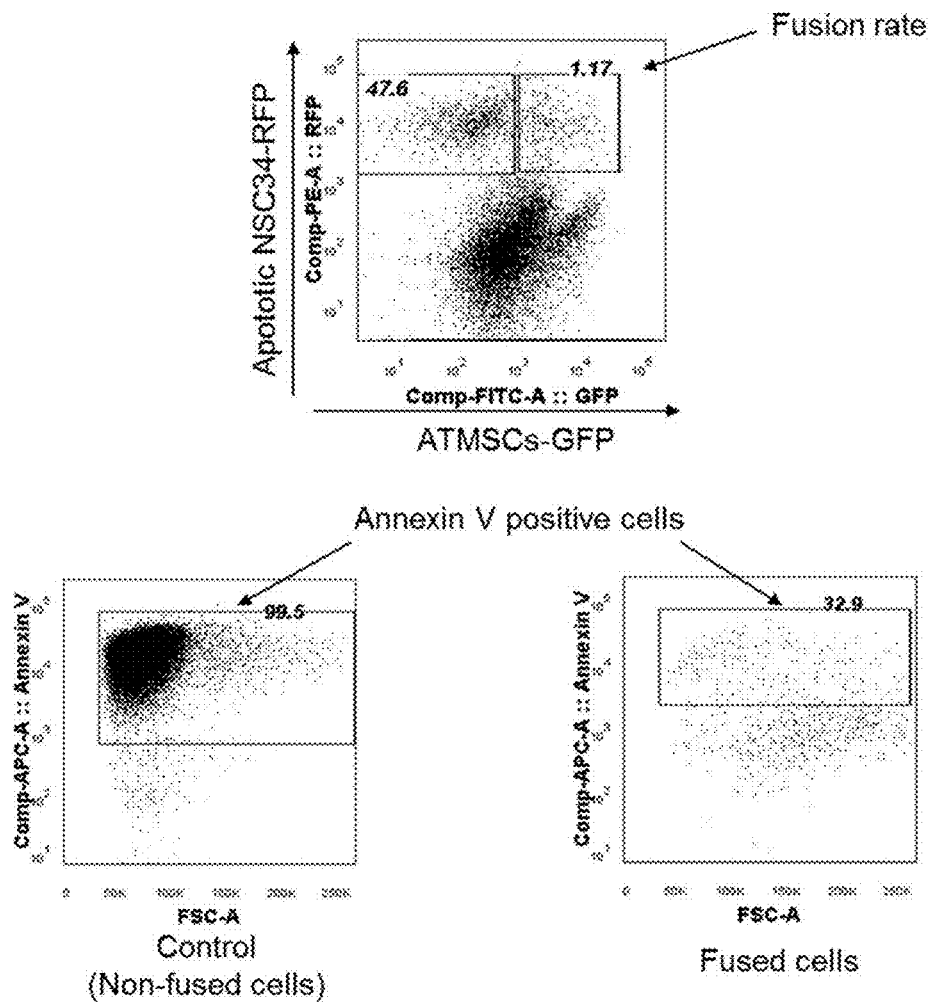
FIG. 1 illustrates an effect of inhibiting cell death of a dying NSC34 motorneuron cell line by cell fusion with hATMSCs according to an exemplary embodiment of the present invention.

Hereinafter, the present invention will be described in detail by the following Examples.

The present invention provides a vector including genes encoding hemagglutinin neuraminidase (HN) and fusion (F) proteins.

In the present invention, the HN and F proteins may be derived from sendai virus, human immunodeficiency virus 1, influenza virus or vesicular stomatitis virus, but is not limited thereto. Various types of HN and F proteins having various origins and/or full lengths and/or fragments may be used as long as these proteins may promote the fusion of cells, inhibit the death, and restore the damage to the damaged cells through the same or similar mechanism as or to these proteins (Eckert D M, Kim P S. Annu Rev Biochem. 2001; 70:777-810; Sapir A, Avinoam O, Podbilewicz B, Chernomordik L V. Dev Cell. 2008 January; 14(1):11-21; Kouris N A, Schaefer J A, Hatta M, Freeman B T, Kamp T J, Kawaoka Y, Ogle B M. Stem Cells Int. 2012; 2012: 414038).

The hemagglutinin neuraminidase (HN) according to the present invention is a glucoprotein expressed in viruses and may exist as a single virus protein having activities of both hemagglutinin and neuraminidase or separate proteins, but is not limited thereto and all of the proteins may be included in the present invention as long as the proteins achieve an effect according to the present invention. Examples of the former may include those derived from paramyxoviruses such as a mumps virus, a sendai virus, a human parainfluenza virus, or an avian Newcastle disease virus and examples of the latter may include those derived from an influenza virus. These proteins and nucleic acid sequences are known, and for example, the hemagglutinin neuraminidase may refer to information in Enzyme entry (http://enzyme.expasy.org) EC:3.2.1.18 and the protein sequences are derived from, for example, sendai viruses and published in GenBank accession no. AAB06288.1. In one embodiment according to the present invention, a sendai virus-derived HN single protein which may be prepared according to a method in Example 2 of the present invention is used.

Further, the F protein is called a glucoprotein which is used in intercellular fusion or fusion/entry of virus into cells, endocytosis, and membrane trafficking. In one embodiment according to the present invention, virus-derived F proteins are used and divided into classes I, II, and III according to structural features. Examples of the class I include GP2 of ebola virus, Mo-55 of moloney murine leukemia virus (MoMuLv), gp41 of immunodeficiency virus HIV, simian virus (SIV) gp41, and the like. Examples of the class II include SFV E1, TBEV E, and the like. Examples of the class III include glycoprotein B (gB) of herpes simplex virus (HSV), gB of epstein-barr virus (EBV), protein G of vesicular stomatitis virus (VSV), glycoprotein gp64 of beculovirus, and the like. Such fusion glycoproteins and nucleic acid sequences are published and for example, published in GenBank Accession no. AAC82300.1.

In the present invention, the genes encoding the HN and F proteins may be used as full-length and/or fragmental types. Particularly, wide-type gene sequences encoding the proteins disclosed in the present invention and fragments thereof include genes in which some of base sequences are artificially modified so that features such as expression in cells or stability of the proteins are advantageous, and naturally found genes in which some of base sequences are modified, or all fragments thereof. The modification of the gene base sequences may include or not modifications of corresponding amino acids, and the modifications of the amino acids include mutants, derivatives, alleles, variants, and homologues, which encode proteins consisting of amino acid sequences in which one or more amino acids are substituted, deleted, added and/or inserted in a protein encoded by the gene causing the modification. When the mutation of the gene base sequences does not include the modification of the amino acids in the protein, the mutation includes, for example, degeneracy mutation, and these degeneracy mutants are included in the gene of the present invention.

The artificial modification of the gene base sequences may be prepared by methods known to those skilled in the art, for example, site-directed mutagenesis (Kramer et al, 1987), error-induced PCR (Cadwell, R. C. and G. F. Joyce. 1992. PCR methods Appl., 2:28-33), point mutation (Sambrook and Russel, Molecular Cloning: A Laboratory Manual, 3rd Ed. 2001, Cold Spring Harbor Laboratory Press), and the like.

In the present invention, the vector means a means for expressing a target gene in host cells. The vector includes elements for expressing the target gene and may include a replication origin, a promoter, an operator gene, a transcription terminator, and the like and may further include a suitable enzyme site (for example, a restrictive enzyme site) for introduction into a genome in the host cells and/or a selection marker for confirming successful introduction into the host cells, and/or a ribosome binding site (RBS) for translation to the protein, an internal ribosome entry site (IRES), and the like. The vector may further include a transcription regulator (for example, an enhancer and the like) in addition to the promoter.

Further, the vector may be a plasmid DNA, a recombinant vector, or other vectors, which are known in the art, and particularly, may be a linear DNA plasmid DNA, a non-viral recombinant vector, a viral recombinant vector, or an inducible gene expression vector system, and the viral recombinant vector may be retroviruses, adenoviruses, adeno-associated viruses, helper-dependent adenoviruses, herpes simplex viruses, lentivirus vectors or vaccinia viruses, but is not limited thereto.

Further, the vector means an expression vector for gene therapy. The term "gene therapy" refers to a method of inserting a normal gene into cells having gene abnormality or proving a new function to normalize its function in order to treat various genetic diseases caused by the gene abnormality. Accordingly, in the present invention, the expression vector for gene therapy means an expression vector which may provide a new function through cell fusion between cells having gene abnormality and normal cells by transferring hemagglutinin neuraminidase (HN)/fusion (F) protein genes into normal cells in the body and therefore normalize its function.

In one embodiment of the present invention, the HN/F protein genes may be introduced into the cells according to the present invention by preparing primers which can specifically recognize the genes from known sequences, amplifying the genes through polymerase chain reaction using the primers, and introducing the amplified genes into the expression vector, as described below. The introduction method is known and for example, may include liposome-mediated transduction, calcium phosphate transduction, DEAE-dextran mediated transduction, positively charged lipid mediated transduction, electroporation, transduction using a phage system, infection using a virus, or the like, but the present invention is not limited thereto.

Further, the present invention provides a cell transformed with a vector including genes encoding hemagglutinin neuraminidase (HN) and fusion (F) proteins.

In the present invention, the term "transformation" means a phenomenon in which a genetic property of a living organism is changed by DNA given from the outside, that is, a genetic trait is changed while DNA is introduced to the cells thereof when DNA, a kind of nucleic acid extracted from cells in any system of the living organism is introduced into living cells in another system.

In the present invention, the transformed cells may be stem cells, progenitor cells, or animal cells, but the present invention is not limited thereto. Further, the stem cells may be particularly embryonic stem cells, adult stem cells, and induced pluripotent stem cells (iPS) and more particularly adult stem cells (mesenchymal stem cells), but the present invention is not limited thereto. Further, the cells may be autologous or allogeneic, or allogenic or xenogenic cells. Most preferably, since the cells are autologous-derived and derived from a recipient, there is no problem in immune response when a pharmaceutical composition is administered and there is an advantage in safety.

The adult stem cells refer to undifferentiated stem cells found in the whole adult even after an embryonic development stage. The adult stem cells have a site-specific differentiation in which the cells themselves are differentiated according to characteristics of surrounding tissues. The adult stem cells may be derived from various adult cells, such as bone marrow, blood, brain, skin, fat, skeletal muscle, umbilical cord, cord blood, and the like. Specific examples thereof may include mesenchymal stem cells (MSC), skeletal muscle stem cells, hematopoietic stem cells, neuronal stem cells, hepatic stem cells, adipose-derived stem cells, adipose-derived progenitor cells, vascular endothelial progenitor cells, and the like, but the present invention is not limited thereto.

In addition, the mesenchymal stem cells are adult stem cells obtained from the respective parts of the body that have already become adult, and refer to pluripotent or multipotent cells capable of differentiating into various cells, for example, adipocytes, motorneuron cells, and the like, as stem cells isolated from cord blood, fat, bone marrow, blood, dermis or periosteum. Further, the mesenchymal stem cells may be effectively engrafted from allogenic or xenogenic recipients without using immune inhibitors. The mesenchymal stem cells may be animal, particularly mammal, and more particularly human mesenchymal stem cells.

In one embodiment of the present invention, the mesenchymal stem cells are stem cells derived from adipose tissue. The mesenchymal stem cells derived from the adipose tissue have a practical advantage of being able to receive a large amount unlike bone marrow, amniotic fluid, and cord blood stem cells, about 1% of the adipocytes has been estimated as the stem cells, and recently, the adipose-derived stem cells are highly useful due to infinite supplyability when considering that a cosmetic surgery widely performed in the advanced countries is liposuction.

A process of obtaining the mesenchymal stem cells will be described as follows. The mesenchymal stem cells are isolated from mammals including humans or mice, preferably human mesenchymal stem cell sources, for example, adipose tissue, blood or bone marrow. Next, the cells are cultured in a suitable medium. In the culture process, the floating cells are removed and the cells attached to a culture plate are subcultured to finally obtain established mesenchymal stem cells.

In addition, a process of isolating and culturing a very small amount of mesenchymal stem cells in bone marrow and the like, is well known in the art, and for example, there is disclosed in U.S. Pat. No. 5,486,359.

As the medium to be used in the above process, any medium generally used for culturing the stem cells may be used. Preferably, the medium is a medium containing serum (for example, fetal bovine serum, horse serum and human serum). The medium to be used in the present invention includes, for example, RPMI series, Eagles's MEM (Eagle's minimum essential medium, Eagle, H. Science 130:432 (1959)), α-MEM (Stanner, C. P. et al., Nat. New Biol. 230:52(1971)), Iscove's MEM (Iscove, N. et al., J. Exp. Med. 147:923(1978)), 199 media (Morgan et al., Proc. Soc. Exp. Bio. Med., 73:1(1950)), CMRL 1066, RPMI 1640 (Moore et al., J. Amer. Med. Assoc. 199:519(1967)), F12 (Ham, Proc. Natl. Acad. Sci. USA 53:288(1965)), F10 (Ham, R. G. Exp. Cell Res. 29:515(1963)), DMEM (Dulbecco's Modified Eagle's medium, Dulbecco, R. et al., VirProcy 8:396(1959)), a mixture of DMEM and F12 (Barnes, D. et al., Anal. Biochem. 102:255(1980)), Way-mo, h's MB752/1 (Waymo, h, C. J. Natl. Cancer Inst. 22:1003 (1959)), McCoy's 5A (McCoy, T. A., et al., Proc. Soc. Exp. Biol. Med. 100:115(1959)) and MCDB series (Ham, R. G. et al., In Vitro 14:11(1978)), but the present invention is not limited thereto. In the media, other ingredients, for example, antibiotics, or antifungal agents (e.g., penicillin, streptomycin), glutamine, and the like may be included. A general description of the media and culture is disclosed in R. Ian Freshney, Culture of Animal Cells, Alan R. Liss, Inc., New York (1984), which is incorporated in this specification by reference.

The mesenchymal stem cells may be confirmed by, for example, a flow cytometry. The flow cytometry is performed by using a specific surface marker of the mesenchymal stem cells. In one embodiment of the present invention, the mesenchymal stem cells according to the present invention have CD29, CD44 and CD90 as markers and phenotypes of CD34, CD45 and HLA-DR as negative markers.

In addition, the inducible pluripotent stem cells can be prepared to multipotent stem cells such as embryonic stem cells by introducing four specific genes that induce dedifferentiation into somatic cells such as skin cells of a non-pluripotent adult, and then expressing the cells or extracting a dedifferentiation inducible protein prepared from the cells introduced with the four genes to inject the extracted protein into somatic cells again, which are called inducible multipotent stem cells or dedifferentiation stem cells. The inducible pluripotent stem cells are used for stem cell therapy using the inducible pluripotent stem cells, cell-based studies in disease model and drug development by producing inducible pluripotent stem cells and differentiating the stem cells in vitro by obtaining somatic cells from patients to study progress of various diseases, and the like.

Further, the progenitor cell is a cell at a stage before the shape and function of a specific cell are established, and is a cell that can be differentiated into cells of a specific cell line or can be formed into a specific type of tissue, and means a cell having self-renewal, but an extremely limited differentiation. Endoderm progenitor cells, mesodermal progenitor cells, and ectoderm precursor cells are all included therein.

Further, the animal cell is a functional and structural basic unit originating from an animal including a human and may be included in the scope of the present invention if it is a cell originating from an animal including a human being (for example, a mammal such as a monkey, a dog, a goat, a pig, a mouse, and the like). Accordingly, the animal cells of the present invention are not limited thereto, but include epithelial cells, endothelial cells, muscular cells, germ cells, skin cells (e.g., fibroblasts, keratinocytes), immune cells, cancer cells and the like. As specific examples, chinese hamster ovary (CHO) cells, mouse myeloma (NSO) cells, baby hamster kidney (BHK) cells, Sp2/0 (mouse myeloma) cells, human retinal cells, HUVEC cells, HMVEC cells, COS-1 cells, COS-7 cells, HeLa cells, HEK-293 cells, HepG-2 cells, HL-60 cells, IM-9 cells, Jurkat cells, MCF-7 cells or T98G cells may be exemplified, but the present invention is not limited thereto.

Further, the present invention provides a pharmaceutical composition for treating cell damage-related diseases including a vector including genes encoding hemagglutinin neuraminidase (HN) and fusion (F) proteins or a cell transformed with the vector.

In the present invention, the vector or the cell transformed with the vector are the same as the description of the vector and the cells, and the detailed description thereof refers to the above contents. Hereinafter, only a specific configuration of the pharmaceutical composition for treating cell damage-related diseases will be described.

In the present invention, the cell damage may be neuronal cell damage or muscular cell damage, and the neuronal cell damage may be caused by neurodegenerative diseases, neurological diseases, degenerative brain diseases, spinal cord injury, peripheral nerve injury, or neuronal cell death and the muscular cell damage may be caused by degenerative muscular disease, muscular diseases, and muscular cell damage due to gene anomalies, but the present invention is not limited thereto.

In the present invention, the cell damage-related diseases may include neurodegenerative diseases, neurological diseases, degenerative muscular diseases, or muscular diseases, but the present invention is not limited thereto.

The neurodegenerative disease or the neurological disease may include Alzheimer's disease (AD), dementia, multi-infarct dementia (MID), frontotemporal dementia, dementia with Lewy bodies, mild cognitive impairment, corticobasal degeneration, Parkinson's disease (PD), multiple system atrophy (MSA), Huntington's disease, spinal muscular atrophy, spinal bulbar muscular atrophy, progressive supranuclear palsy (PSP), metabolic brain disease, depression, epilepsy, dentatorubropallidoluysian atrophy (DRPLA), spinocerebellar ataxia, amyotrophic lateral sclerosis (ALS), multiple sclerosis, primary lateral sclerosis, progressive bulbar palsy, glaucoma, stroke, brain ischemia, post-encephalitic parkinsonism, Tourette's syndrome, restless legs syndrome, or attention deficit disorders with hyperactivity, but the present invention is not limited thereto.

The degenerative muscular disease or the muscular disease may include myopathy, congenital myopathy, congenital muscular dystrophy, Duchenne muscular dystrophy, Becker muscular dystrophy, Limb Girdle muscular dystrophy, facioscapulohumeral muscular dystrophy, oculopharyngeal muscular atrophy, distal muscular dystrophy, Emery-Dreifuss muscular dystrophy, myotonic dystrophy, Barth syndrome, heart failure, or X-linked dilated cardiomyopathy, but the present invention is not limited thereto.

In the present invention, since it is confirmed that the cells overexpressing the HN/F proteins promote cell fusion with other cells by the HN/F proteins, a normal gene is transferred and expressed through fusion with the damaged cells, and the expression of the gene for restoring the cell damage is regulated, the vector including the genes encoding the HN/F proteins or the cell transformed with the vector may be usefully used to reduce and/or restore the cell damage in diseases causing cell damage and gene abnormality, such as neurodegenerative diseases or degenerative muscular diseases.

The pharmaceutical composition according to the present invention may be formulated in a suitable form together with a pharmaceutically acceptable carrier which is generally used. The pharmaceutically acceptable carrier may include, for example, water, suitable oils, saline, parenteral administration carries such as aqueous glucose and glycol, and the like, and further include stabilizers and preservatives. The suitable stabilizer includes an antioxidant such as sodium hydrogen sulfite, sodium sulfite, or ascorbic acid. The suitable preservative includes benzalcohol chloride, methyl- or propyl-paraben, and chlorobutanol. In addition, the composition for cell therapy according to the present invention may suitably include suspending agents, solubilizers, stabilizers, isotonizing agents, preservatives, adsorption inhibitors, surfactants, diluents, excipients, pH adjusters, analgesic agents, buffers, antioxidants, and the like according to the administration method or the formulation, if necessary. The pharmaceutically acceptable carriers and formulations suitable for the present invention, including those exemplified above, are described in detail in the document [Remington's Pharmaceutical Sciences, latest edition].

The pharmaceutical composition of the present invention is formulated by using a pharmacologically acceptable carrier and/or excipient according to a method that may be easily performed by those skilled in the art to be prepared in a unit dosage form or prepared by intrusion into a multi-dose container.

Further, the pharmaceutical composition may also be administered by any device in which active ingredients may move to the target cell. The pharmaceutical composition of the present invention may be included with a therapeutically effective dose for treatment of diseases. In the present invention, the term "treatment' means reversing or mitigating one or more symptoms of a disease or a disorder to which the term is applied, or inhibiting or preventing the progress thereof, unless otherwise stated. The term "therapeutically effective dose" means an amount of an active ingredient or a pharmaceutical composition which induces a biological or medical response in tissue systems, animals, or humans which is considered by researchers, veterinarian, physician, or other clinicians, and includes an amount of inducing mitigation of symptoms of diseases or disorders to be treated. It is apparent to those skilled in the art that the active ingredients included in the pharmaceutical composition of the present invention are changed according to an effect.

Therefore, the optimal content of the pharmaceutical composition may be easily determined by those skilled in the art, and may be adjusted according to various factors including a type of disease, severity of the disease, contents of other ingredients contained in the composition, a type of formulation, and an age, a weight, a general health condition, a gender, and a diet of a patient, an administration time, a administration route, a secretion ratio of the composition, a treatment period, and simultaneously used drugs.

In one embodiment of the present invention, the pharmaceutical composition is administered intravenously or intrathecally.

It is important to include an amount capable of obtaining a maximum effect by a minimum amount without side effects by considering all of the factors. For example, the dose of the composition of the present invention may be $0.1\times10^5$ to $1.0\times10^8$ cells/kg (body weight) and more preferably $0.5\times10^6$ to $1.0\times10^7$ cells/kg (body weight) of a cell transformed with the vector including the genes encoding the HN and F proteins as active ingredients. However, the dose thereof may be variously prescribed by factors such as a formulation method, an administration type, age, weight, and gender of a patient, a pathological condition, food, an administration time, an administration route, an excretion rate, and response susceptibility, and those skilled in the art may suitably adjust the dose by considering the factors. The number of administrations may be one or two times within a range of clinically acceptable side effects, and even in administration sites, the composition may also be administered to one site or two or more sites. Even in the animals other than the human, the same dose as that of the human per kg may be administered, or an amount obtained by converting the dose by, for example, a volume ratio (for example, an average value) in ischemic organs (heart and the like) between target animal and human and the like may be administered. Examples of the animal to be treated according to the present invention may include humans, and mammals for other purposes, and particularly, include humans, monkeys, mice, rats, rabbits, sheep, cows, dogs, goats, horses, pigs, and the like.

Further, the present invention provides a method for reducing cell damage including: administering a vector including genes encoding hemagglutinin neuraminidase (HN) and fusion (F) proteins or a cell transformed with the vector to a subject, with a therapeutically effective dose.

In the present invention, the vector or the cell transformed with the vector, the administration method and the dose thereof, and the like are described the same as those of the vector, the cells, and the administration method and the dose of the pharmaceutical composition including the same, and thus, the detailed description will be based on the contents.

In the present invention, the cell damage may be neuronal cell damage or muscular cell damage, and the neuronal cell damage may be caused by neurodegenerative diseases, neurological diseases, degenerative brain diseases, spinal cord injury, peripheral nerve injury, or neuronal cell death and the muscular cell damage may be caused by degenerative muscular diseases, muscular diseases, and muscular cell damage due to gene anomalies, but the present invention is not limited thereto.

In the present invention, the subject is a subject that suffers from the neurodegenerative diseases, the neurological diseases, the degenerative muscular diseases, or the muscular diseases, and the more particularly, includes mammals, for example, humans, monkeys, mice, rats, rabbits, sheep, cows, dogs, goats, horses, pigs, and the like, which are administered with the vector including the genes encoding the HN and F proteins or the cell transformed with the vector to mitigate and/or restore the cell damage caused by the diseases, for example, the neuronal cell damage or the muscular cell damage.

The neurodegenerative disease or the neurological disease may include Alzheimer's disease (AD), dementia, multi-infarct dementia (MID), frontotemporal dementia, dementia with Lewy bodies, mild cognitive impairment, corticobasal degeneration, Parkinson's disease (PD), multiple system atrophy (MSA), Huntington's disease, spinal muscular atrophy, spinal bulbar muscular atrophy, progressive supranuclear palsy (PSP), metabolic brain disease, depression, epilepsy, dentatorubropallidoluysian atrophy (DRPLA), spinocerebellar ataxia, amyotrophic lateral sclerosis (ALS), multiple sclerosis, primary lateral sclerosis, progressive bulbar palsy, glaucoma, stroke, brain ischemia, post-encephalitic parkinsonism, Tourette's syndrome, or attention deficit disorders with hyperactivity, but the present invention is not limited thereto.

In addition, the degenerative muscular disease or the muscular disease may include myopathy, congenital myopathy, congenital muscular dystrophy, Duchenne muscular dystrophy, Becker muscular dystrophy, Limb Girdle muscular dystrophy, facioscapulohumeral muscular dystrophy, oculopharyngeal muscular atrophy, distal muscular dystrophy, Emery-Dreifuss muscular dystrophy, myotonic dystrophy, Barth syndrome, heart failure, or X-linked dilated cardiomyopathy, but the present invention is not limited thereto.

In the present invention, since it is confirmed that the cells overexpressing the HN/F proteins promote cell fusion with other cells by the HN/F proteins, a normal gene is transferred and expressed through fusion with the damaged cells, and the expression of the gene restoring the cell damage is regulated, the vector including the genes encoding the HN/F proteins or the cell transformed with the vector may be usefully used to reduce/or restore cell damage caused by neurodegenerative diseases, neurological diseases, degenerative brain diseases, spinal cord injury, peripheral nerve injury, neuronal cell death, degenerative muscular diseases, muscular diseases, muscular cell damage due to gene abnormality, or the like.

Further, the present invention provides a method for treating neurodegenerative diseases or neurological diseases including: administering a vector including genes encoding hemagglutinin neuraminidase (HN) and fusion (F) proteins or a cell transformed with the vector to a subject, with a therapeutically effective dose.

In the present invention, the vector or the cell transformed with the vector, the administration method and the dose thereof, and the like are described the same as those of the vector, the cells, and the administration method and the dose of the pharmaceutical composition including the same, and thus the detailed description will be based on the contents.

In the present invention, the neurodegenerative disease or the neurological disease may include Alzheimer's disease (AD), dementia, multi-infarct dementia (MID), frontotemporal dementia, dementia with Lewy bodies, mild cognitive impairment, corticobasal degeneration, Parkinson's disease (PD), multiple system atrophy (MSA), Huntington's disease, spinal muscular atrophy, spinal bulbar muscular atrophy, progressive supranuclear palsy (PSP), metabolic brain disease, depression, epilepsy, dentatorubropallidoluysian atrophy (DRPLA), spinocerebellar ataxia, amyotrophic lateral sclerosis (ALS), multiple sclerosis, primary lateral sclerosis, progressive bulbar palsy, glaucoma, stroke, brain ischemia, post-encephalitic parkinsonism, Tourette's syndrome, restless legs syndrome, or attention deficit disorders with hyperactivity, but the present invention is not limited thereto.

In the present invention, since it is confirmed that the cells overexpressing the HN/F proteins promote cell fusion with other cells by the HN/F proteins, a normal gene is transferred and expressed through fusion with the damaged cells, and the expression of the gene restoring the cell damage is regulated, the vector including the genes encoding the HN/F proteins or the cell transformed with the vector may be usefully used to treat neurodegenerative diseases or neurological diseases.

Further, the present invention provides a method for treating degenerative muscular diseases or muscular diseases including: administering a vector including genes encoding hemagglutinin neuraminidase (HN) and fusion (F) proteins or a cell transformed with the vector to a subject, with a therapeutically effective dose.

In the present invention, the vector or the cell transformed with the vector, the administration method and the dose thereof, and the like are described the same as those of the vector, the cells, and the administration method and the dose of the pharmaceutical composition including the same, and thus the detailed description will be based on the contents.

The degenerative muscular disease or the muscular disease may include myopathy, congenital muscular dystrophy, Duchenne muscular dystrophy, Becker muscular dystrophy, Limb Girdle muscular dystrophy, facioscapulohumeral muscular dystrophy, oculopharyngeal muscular atrophy, distal muscular dystrophy, Emery-Dreifuss muscular dystrophy, myotonic dystrophy, Barth syndrome, heart failure, or X-linked dilated cardiomyopathy, but the present invention is not limited thereto.

In the present invention, since it is confirmed that the cells overexpressing the HN/F proteins promote cell fusion with other cells by the HN/F proteins, a normal gene is transferred and expressed through fusion with the damaged cells, and the expression of the gene restoring the cell damage is regulated, the vector including the genes encoding the HN/F proteins or the cell transformed with the vector may be usefully used to treat degenerative muscular diseases or the muscular diseases.

Hereinafter, the present invention will be described in detail by the following Examples. However, the following Examples just exemplify the present invention, and the contents of the present invention are not limited to the following Examples.

EXAMPLE

Cell Culture

Human adipose tissue-derived mesenchymal stem cells (hATMSCs) obtained by agreement and understanding of the K-STMECELL institutional review board (IRB) were cultured in a RKCM culture medium (added with 10% FBS and provided from the K-STEMCELL) added with antibiotics. A mouse motorneuron cell line (NSC34 Motor Neuron-Like Hybrid Cell line, CEDARLANE, USA) was cultured in a Dulbecco's Modified Eagle's medium (DMEM) (added with 10% FBS) added with antibiotics. A mouse neuroblastoma cell line (N2A cell line, ATCC) was cultured in an Eagle's Minimum Essential medium (EMEM) (added with 10% FBS) added with antibiotics. A human cervical cancer cell line (HeLa cell line, ATCC) was cultured in an Eagle's Minimum Essential medium (EMEM) (added with 10% FBS) added with antibiotics. All of the cells were cultured at 37° C. under 5% $CO_2$ supply.

Example 1. Analysis of Apoptosis Inhibition Effect in Motorneuron Cell Line by Cell Fusion Between Dying Motorneuron Cell Line and Adipose-Derived Mesenchymal Stem Cells Motorneuron cell line NSC34 cells marked with a cell tracker CM-DiI (Thermofisher) were treated with 2.5 μM of thapsigargin as an apoptosis inducer and then cultured for 24 hours. After Annexin V staining, annexin V-positive NSC34 cells were isolated using an annexin V antibody by a flow cytometry. hATMSCs and annexin V-positive NSC34 cells marked with a green dye (Cell-Stalker™, Biterials) were fused using a Sendai virus (HVJ) envelope cell fusion kit (GenomONE™-CF EX Envelope Cell Fusion Kit, COSMO BIO, Japan) according to a manufacturer's method, and then V-positive cells were analyzed using a flow cytometry. As shown in FIG. 1, 99.5% of annexin V-positive cells were found in a group of NSC34 cells which were not fused with the hATMSCs, and 32.9% of annexin V-positive cells were found in a group of NSC34 cells which are fused with the hATMSCs. Such a result indicates that the death of the NSC34 motorneuron cell line may be inhibited by the cell fusion with the hATMSCs.

Figure 2:
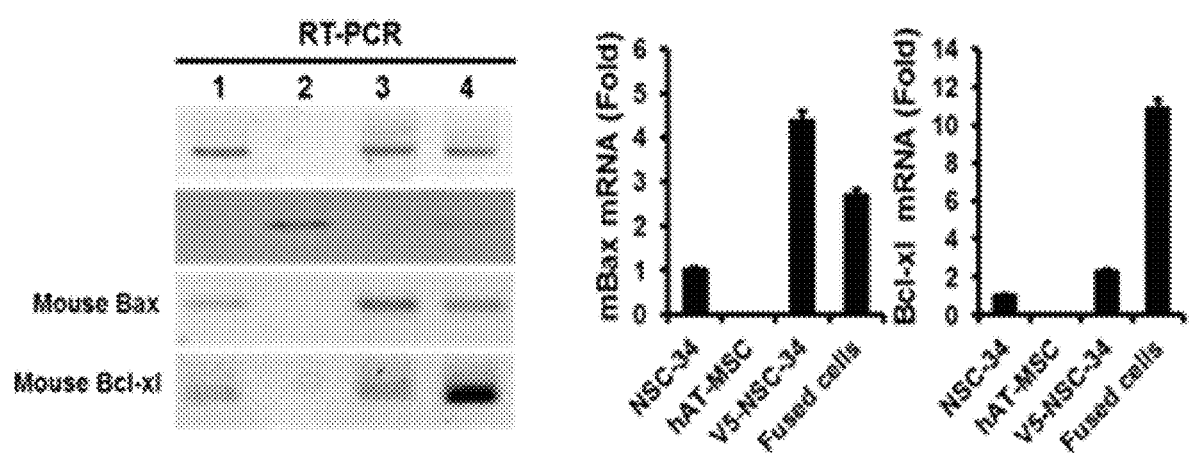
FIG. 2 illustrates an expression analysis of Bax and Bcl-xL in a NSC34 cells, hATMSCs, apoptotic NSC34 cells and fused cells (apoptotic NSC-34 cells with hATMSCs) according to the exemplary embodiment of the present invention.
Figure 3:
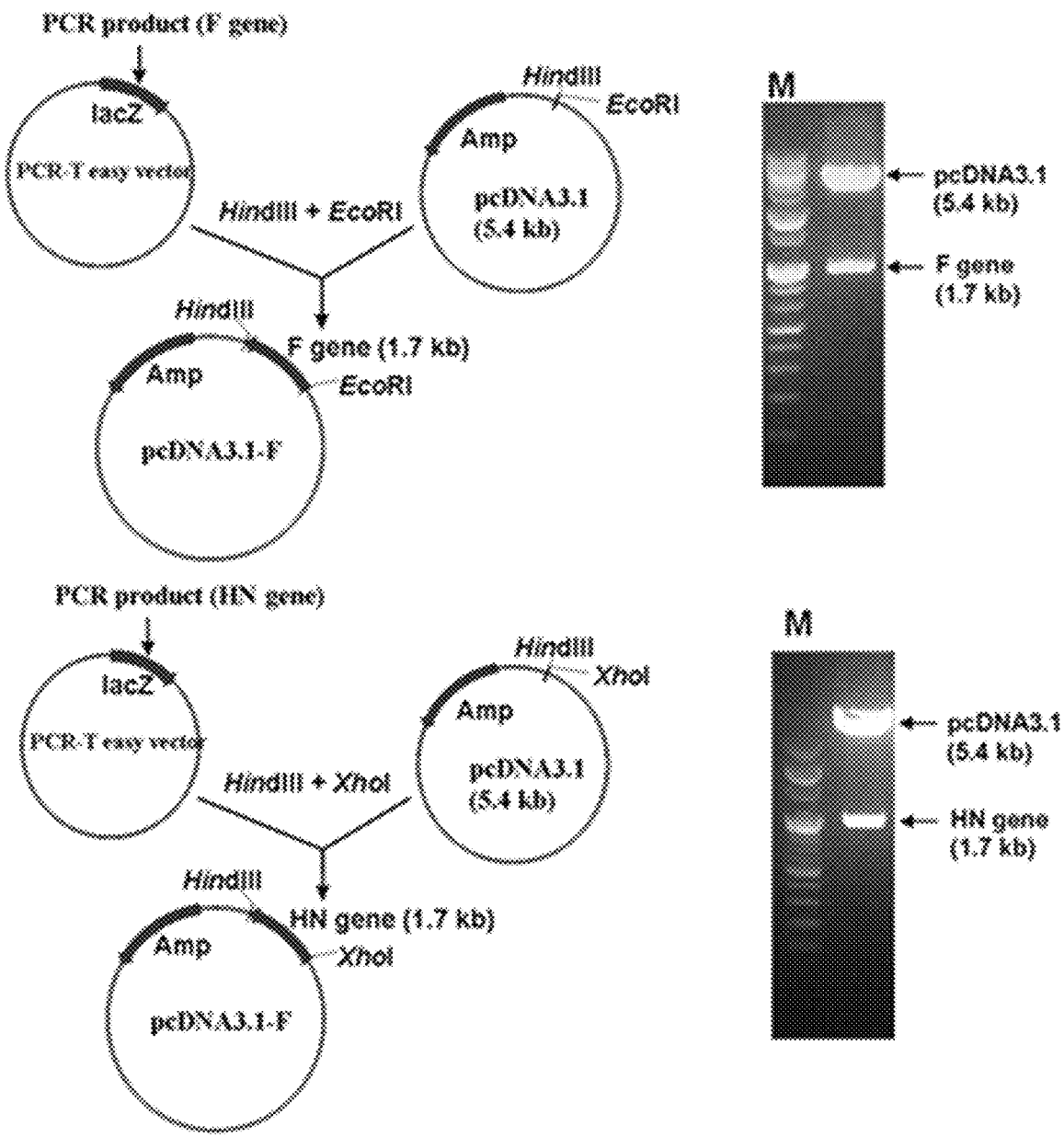
FIG. 3 is a schematic diagram for preparing expression vectors inserted with HN and F according to the exemplary embodiment of the present invention.

Further, the apoptosis inhibition effect was confirmed at a molecular level. In summary, the NSC34 cell group which was fused with the hATMSCs was isolated through the flow cytometry and then expression of a pro-apoptotic gene Bax and an anti-apoptotic gene Bcl-xL was analyzed by reverse transcription polymerase chain reaction (RT-PCR) and quantitative RT-PCR. As shown in FIG. 2, as compared with the NSC34 cell group which was not fused with the hATMSCs, in the NSC34 cell group which was fused with the hATMSCs, the expression of Bax mRNA was significantly decreased and the expression of Bcl-xL mRNA was significantly increased.

Such a result indicates that apoptosis is inhibited through the decrease in expression of the pro-apoptotic gene Bax and the increase in expression of the anti-apoptotic gene Bcl-xL when the dying NSC34 motorneuron cell line was fused with the hATMSCs.

Example 2. Preparation of Human Adipose-Derived Mesenchymal Stem Cells (HN/F-hATMSCs) Overexpressing Hemagglutinin Neuraminidase (HN)/Fusion (F) Proteins Genes of hemagglutinin neuraminidase (HN) and F protein (F) were amplified by PCR using a Sendai virus genome as a template and a primer shown in Table 1. The amplified DNAs were inserted into a pcDNA3.1 expression vector, respectively, and cloned in E. coli stain DH5a to confirm a sequence (the result was not shown). The cloned HN and F proteins are the same as published sequences GenBank Accesssion No. AAB06288.1 and AAC82300.1, respectively.

TABLE 1

Primer sequence used in cloning of HN and F genes used in the present invention

| Target gene | Primer sequences | Product size (bp) |
|---|---|---|
| HN FP | 5'-AAGCTTATGGAACAAAAACTCAT CTCAGAAGAGGATCTGGATGGTGATA GGGGCAAACGTGACTCGTACTGG-3' | 1731 |
| HN RP | 5'-GAATTCTCATCTTTTCTCAGCCA TTGCATCAAACCCACC-3' | |
| F FP | 5'-AAGCTTATGCATCATCATCATCA TCATACAGCATATATCCAGAGATCAC AGTGCATCTC-3' | 1704 |
| F RP | 5'-GAATTCTCATCTTTTCTCAGCCA TTGCATCAAACCCACC-3' | |
| Partial HN FP | 5'-CGATCTCTGGATGTGTTAG-3' | 411 |
| Partial HN RP | 5'-CCACACTAGGGTATAATGC-3' | |
| Partial F FP | 5'-CTCATGATAACTGTGGACTC-3' | 402 |
| Partial F RP | 5'-GGTTCAGTAGGCTCTTATAC-3' | |
| Human GAPDH FP | 5'-AGAAGGCTGGGGCTCATTTG-3' | 198 |
| Human GAPDH RP | 5'-AGGGGCCATCCACAGTCTTC-3' | |

The clone obtained after cloning was amplified and cultured in an LB liquid medium for 24 hours, and a plasmid was extracted using a plasmid extraction kit (Midiprep kit) (Invitrogen, USA), and then transduced into hATMSCs using a liposome (lipofectamine 3000, Invitrogen) in a manufacturer's method to obtain hATMSCs (HN/F-hATMSCs) into which the HN/F genes were introduced. Total RNAs were extracted from the transduced cell line and the expression of the HN and F genes was analyzed by RT-PCR and quantitative RT-PCR. The hATMSCs were used as a control group. Partial HN and F primers were used for confirming expression of HN or F mRNA using RT-PCR and quantitative RT-PCR.

Figure 4:
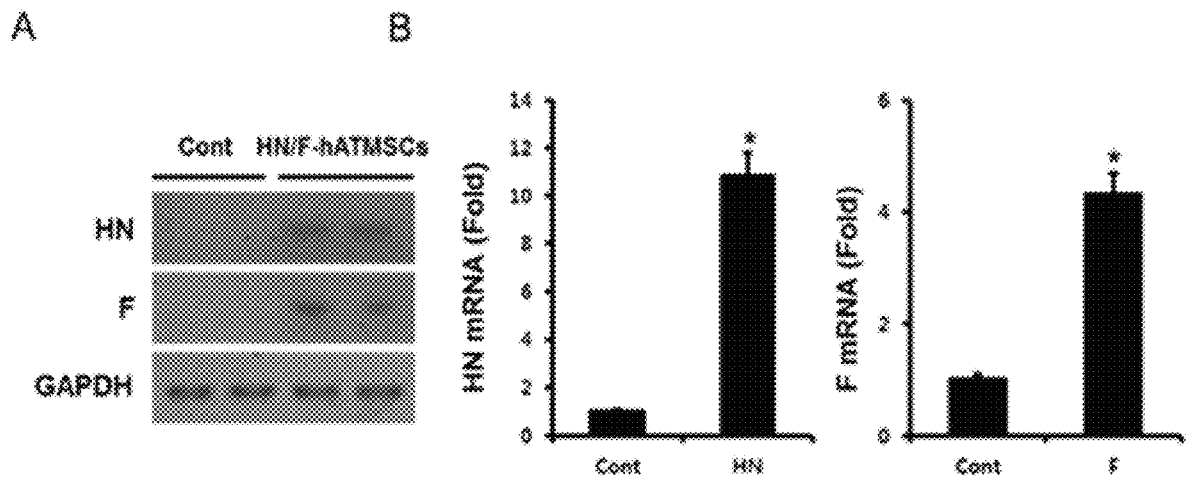
FIG. 4 illustrates an analysis of expression of HN and F mRNAs in HN/F-hATMSCs according to the exemplary embodiment of the present invention.

As the expression analysis result, as shown in FIG. 4, the overexpression of the HN and F genes was confirmed. Such a result indicates that the HN and F genes are successfully overexpressed through liposomal transfection at the same time.

In addition, as shown in Table 1, a base sequence encoding a myc protein was attached to a forward primer for amplifying the HN gene and a base sequence encoding histidine was attached to a forward primer for amplifying the F gene. Thus, the expression of the HN and F proteins was analyzed in the HN/F-hATMSCs using antibodies against the myc protein and the histidine (Santcruz Biotechnology, USA) by a confocal laser microscope (Nicon, Japan).

Figure 5:
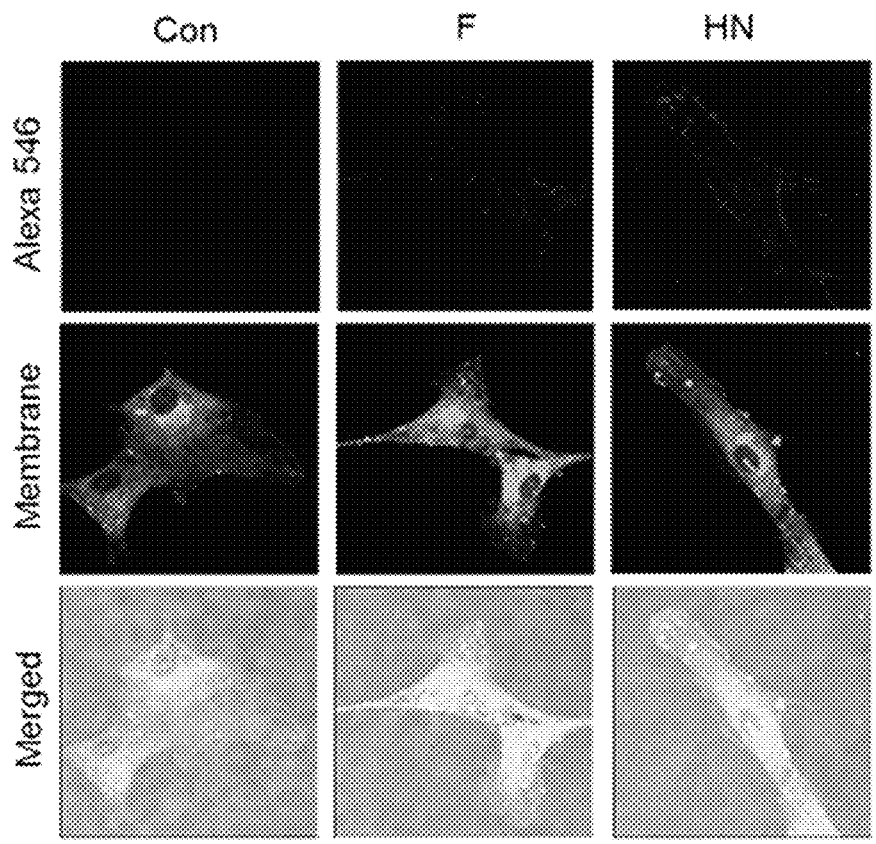
FIG. 5 illustrates an imaging analysis of expression of HN and F proteins in HN/F-hATMSCs according to the exemplary embodiment of the present invention.

As a result of image analysis, as shown in FIG. 5, it was confirmed that the HN and F proteins were expressed on a cell surface of HN/F-hATMSCs. These results indicate that the human adipose-derived mesenchymal stem cells overexpressing the HN and F proteins are successfully prepared.

Example 3. Evaluation of Expression of Stem Cell Markers in HN/F-hATMSCs

Figure 6:
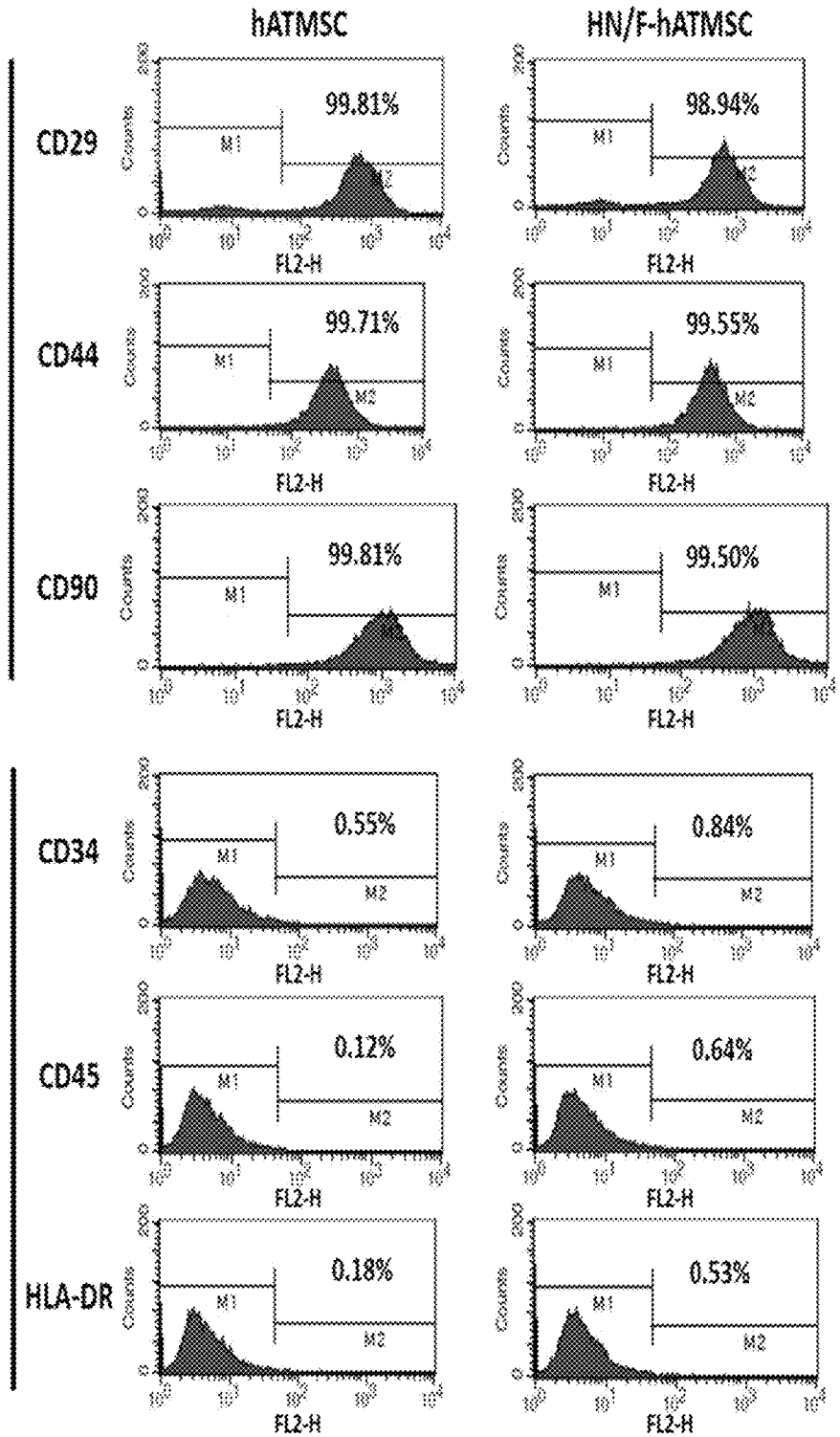
FIG. 6 illustrates an immunophenotyping analysis of HN/F-hATMSCs according to the exemplary embodiment of the present invention.

The expression for adipose-derived mesenchymal stem cell markers in HN/F-hATMSCs was analyzed using antibodies (Santcruz Biotechnology, USA) against positive markers CD29, CD44 and CD90 and negative markers CD34, CD45 and HLA-DR of the adipose-derived mesenchymal stem cells by a flow cytometry. The hATMSCs were used as a control group. As a result of expression analysis, as shown in FIG. 6, it was confirmed that there was no difference in expression between the positive markers CD29, CD44 and CD90 and the negative markers CD34, CD45 and HLA-DR as compared with the control group. These immunophenotyping results indicate that the hATMSCs introduced with the HN and F genes maintain properties of the stem cells.

Figure 7:
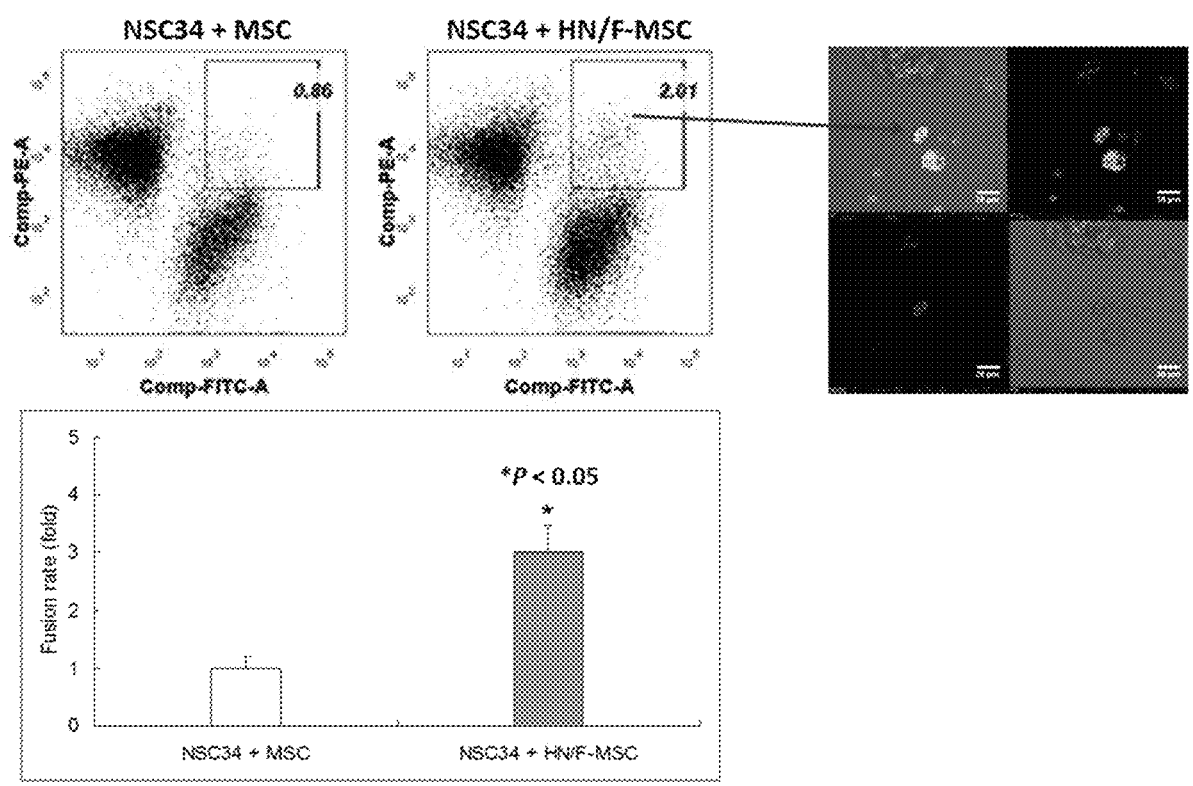
FIG. 7 illustrates an analysis of cell fusion ability with a NSC34 motorneuron cell line in HN/F-hATMSCs according to the exemplary embodiment of the present invention.

Example 4. Evaluation of Cell Fusion Ability of HN/F-hATMSCs and NSC34 Motorneuron Cell Line In order to evaluate the cell fusion ability of the HN/F-hATMSCs prepared in Example 2, a fusion assay of the HN/F-hATMSCs marked with a green dye and a NSC34 motoneuron cell line marked with a cell tracker CM-DiI was performed. Two types of cells were mixed in a 1.5 ml test tube at a cell number ratio of 1:1, reacted at 4° C. for 5 minutes, and then reacted in a 37° C. cell incubator for 15 minutes. The cells were transferred to a 6-well plate containing a DMEM culture medium (added with 10% FBS) added with antibiotics and then cultured at 37° C. under 5% $CO_2$ supply for 16 hours. The cells were collected and a cell fusion rate of the HN/F-hATMSCs and the NSC34 motoneuron cell line was analyzed using a flow cytometry. The hATMSCs were used as a control group. As a result, as shown in FIG. 7, it was confirmed that the cell fusion rate of the HN/F-hATMSCs and the NSC34 motoneuron cell line was increased by 3.5 times or more compared to the control group. Such a result indicates that the cell fusion rate of the HN/F-hATMSCs and the NSC34 motoneuron cell line is increased.

In addition, an image of fused cells of the HN/F-hATMSCs showing green fluorescence and the NSC34 motorneuron cell line showing red fluorescence may be confirmed by an image analysis through a confocal laser microscope, as shown in FIG. 7.

Figure 8:
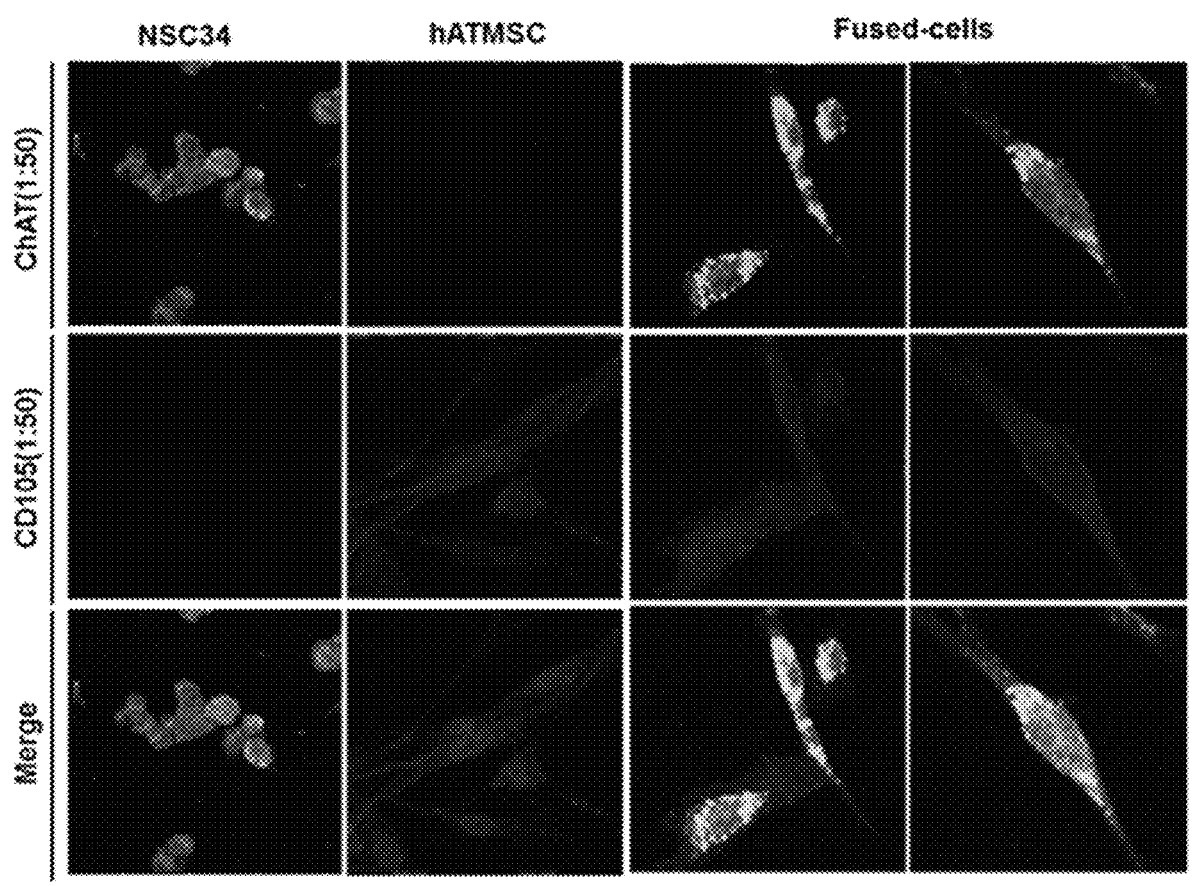
FIG. 8 illustrates an analysis of expression of ChAT and CD105 in fused cells of the NSC34 motorneuron cell line and the HN/F-hATMSCs according to the exemplary embodiment of the present invention.

Example 5. Expression Analysis of Marker of hATMSCs and Marker of Motorneuron Cells in Fused Cells of HN/F-hATMSCs and NSC34 Motorneuron Cell Line For the fused cells of Example 4, the expression of adipose-derived mesenchymal stem cell markers ChAT and CD105 was analyzed by a confocal laser microscope using antibodies (Santcruz Biotechnology, USA) against choline acetyltransferase (ChAT) as an motoneuron cell marker and an adipose-derived mesenchymal stem cell marker CD105. As a result, as shown in FIG. 8, the expression of the motoneuron cell marker ChAT and the adipose-derived mesenchymal stem cell marker CD105 was confirmed in the fused cells of the HN/F-hATMSCs and the NSC34 motorneuron cell line.

These results confirm that the HN/F-hATMSCs and the NSC34 motorneuron cell line were fused, and indicate that the fused cells express all of the marker proteins expressed in the adipose-derived mesenchymal stem cells and the motorneuron cell line.

Figure 9:
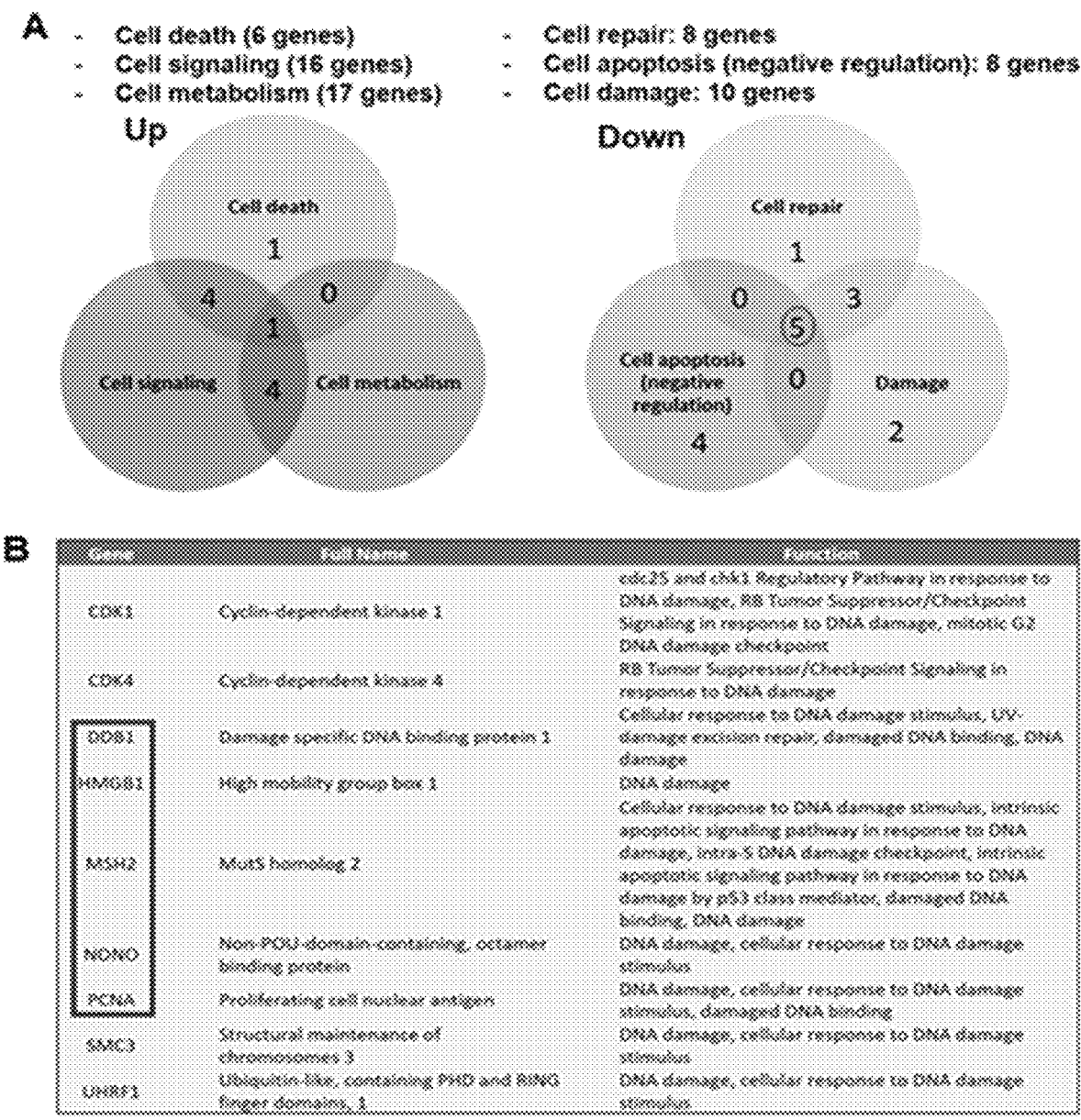
FIG. 9 illustrates a proteomic analysis result among the NSC34 motorneuron cell line, the dying NSC34 motorneuron cell line, and the fused cell line (dying NSC 34 with the HN/F-hATMSCs) according to the exemplary embodiment of the present invention.
Figure 10:
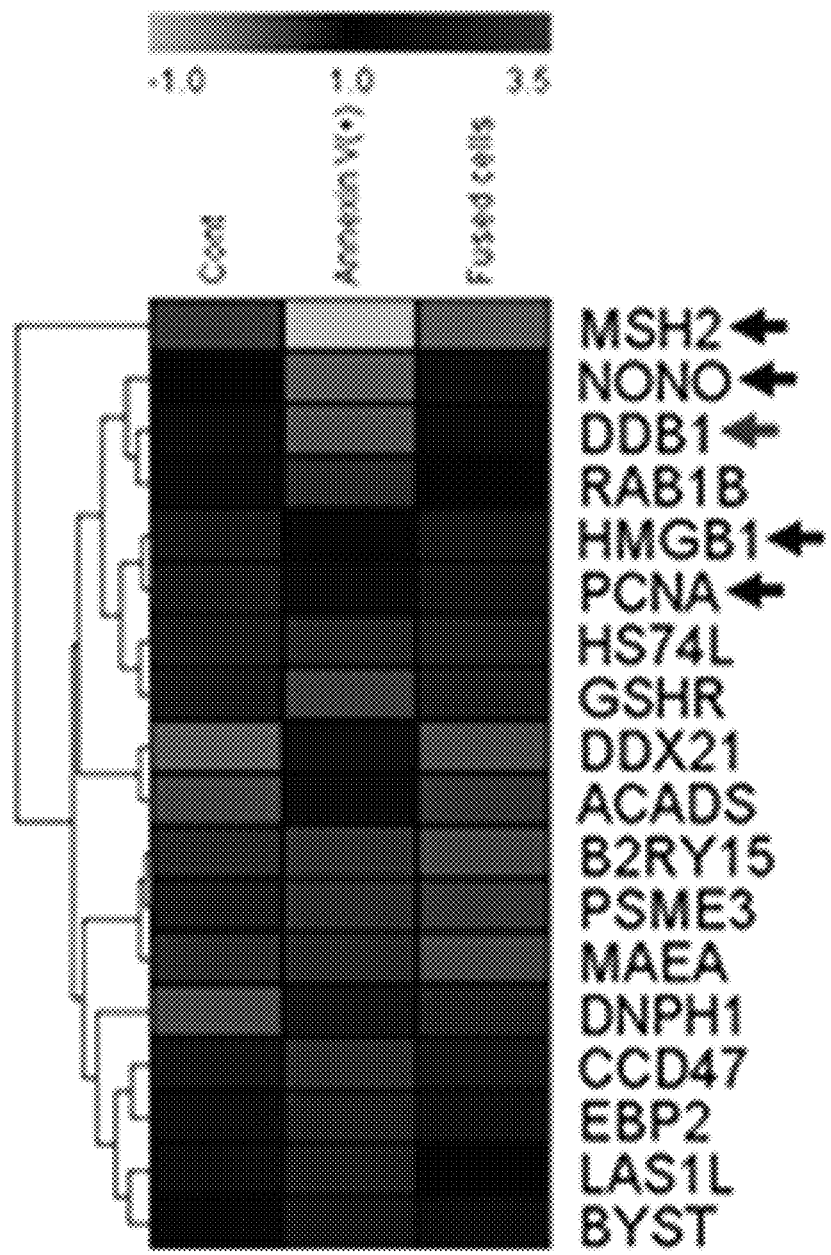
FIG. 10 illustrates a heatmap analysis result among the NSC34 motorneuron cell line, the dying NSC34 motorneuron cell line, and the fused cell line (dying NSC 34 with the HN/F-hATMSCs) according to the exemplary embodiment of the present invention.

Example 6. Proteomics Analysis of Dying NSC34 Motorneuron Cell Line and Fused Cells of HN/F-hATMSCs and NSC34 Motorneuron Cell Line In order to find a cell damage repair mechanism through cell fusion of dying motorneuron cells and HN/F-hATMSCs, a proteomics analysis for the annexin V-positive NSC34 motorneuron cell line in Example 2 and the fused cells in Example 4 was performed using ESI-LTQ-Orbitrap (Termo Fiher) and nanoHPLC (RSLC, Dionex), and a heatmap analysis was performed using MeV software. The NSC34 motorneuron cell line was used as a control group. As the analysis result, as shown in FIGS. 9 and 10, it was confirmed that five genes DDB1, HMGB1, MSH2, NONO and PCNA related with cell repair were decreased in the dying NSC34 motorneuron cells, but increased in the fused cells of the HN/F-hATMSCs and the NSC34 motor neuron cell line, and thus, the five genes were selected as cell damage repair target genes.

Figure 11:
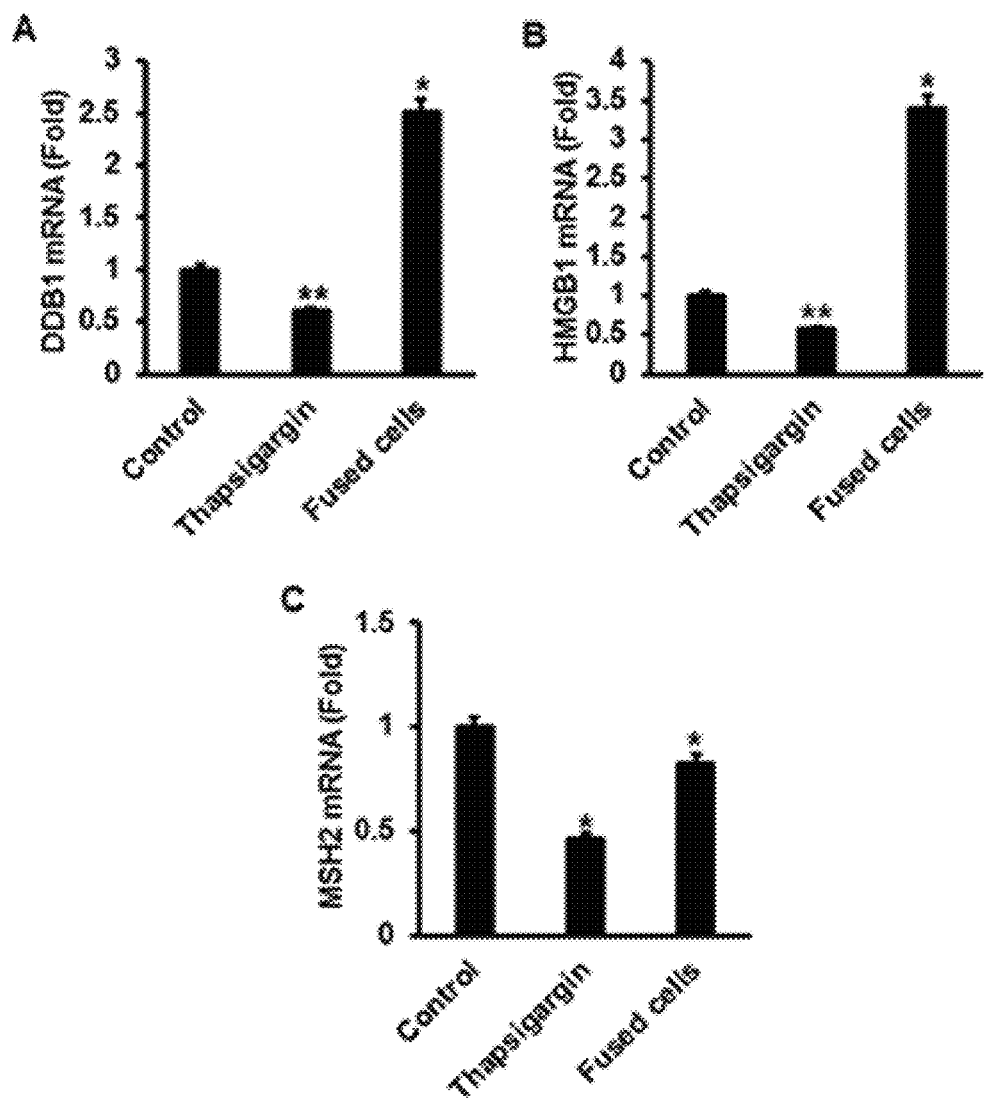
FIG. 11 illustrates an analysis of expression of genes DDB1, HMGB1, and MSH2 mRNAs related with cell repair in the NSC34 motorneuron cell line, the dying NSC34 motorneuron cell line, and the fused cell line (dying NSC 34 with the HN/F-hATMSCs) according to the exemplary embodiment of the present invention.

In addition, a change in expression of DDB1, HMGB1 and MSH2 among the five genes DDB1, HMGB1, MSH2, NONO and PCNA related with the cell repair in the annexin V-positive NSC34 motorneuron cell line of Example 2 and the fused cells of Example 4 was confirmed. In summary, the expression of DDB1, HMGB1 and MSH2 was analyzed through RT-PCR and quantitative RT-PCR in the annexin V-positive NSC34 motorneuron cell line of Example 2 and the fused cells of Example 4. The NSC34 motorneuron cell line was used as a control group. As shown in FIG. 11, the expression of DDB1, HMGB1, and MSH2 mRNAs was decreased in the dying NSC34 motorneuron cell line, but was significantly increased in the fused cells of the HN/F-hATMSCs and the NSC34 motorneuron cell line.

These results indicate that in the process in which the hATMSCs overexpressing the HN and F proteins are fused with the dying NSC34 motorneuron cell line to restore the cell damage, the DDB1, HMGB1, and MSH2 are involved.

Figure 12:
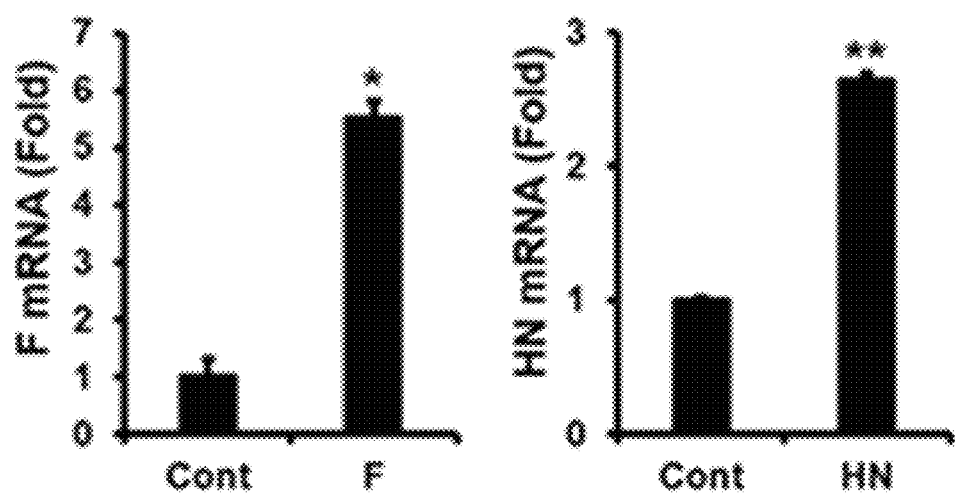
FIG. 12 illustrates an analysis of expression of HN and F mRNAs in HN/F-heLa according to an exemplary embodiment of the present invention.

Example 7. Evaluation of Cell Fusion Ability of N2A Neuroblastoma Cell Line and HeLa Cell Line HN/F-HeLa Overexpressing Hemagglutinin Neuraminidase (HN)/Fusion (F) Proteins In order to find whether a cell fusion ability is shown even in a general cell line overexpressing HN and F proteins, a HeLa cell line HN/F-HeLa overexpressing the HN and F proteins was prepared. In summary, a pcDNA3.1 expression vector inserted with GFP-HN was cloned using a GFP-pcDNA3.1 expression vector and the HN protein gene clone obtained in Example 2. In addition, a pcDNA3.1 expression vector inserted with a RFP-F protein was cloned using a RFP-pcDNA3.1 expression vector and the F protein gene clone obtained in Example 2. Thereafter, a liposome (lipofectamine 3000, Invitrogen) was transduced into HeLa cells according to a manufacturer's method to obtain HeLa (HN/F-HeLa) introduced with HN/F genes. Total RNAs were extracted from the transduced cell line and the expression of the HN and F genes was analyzed by RT-PCR and quantitative RT-PCR. The HeLa cell line was used as a control group. As the expression analysis result, as shown in FIG. 12, the overexpression of the HN and F genes was confirmed.

Figure 13:
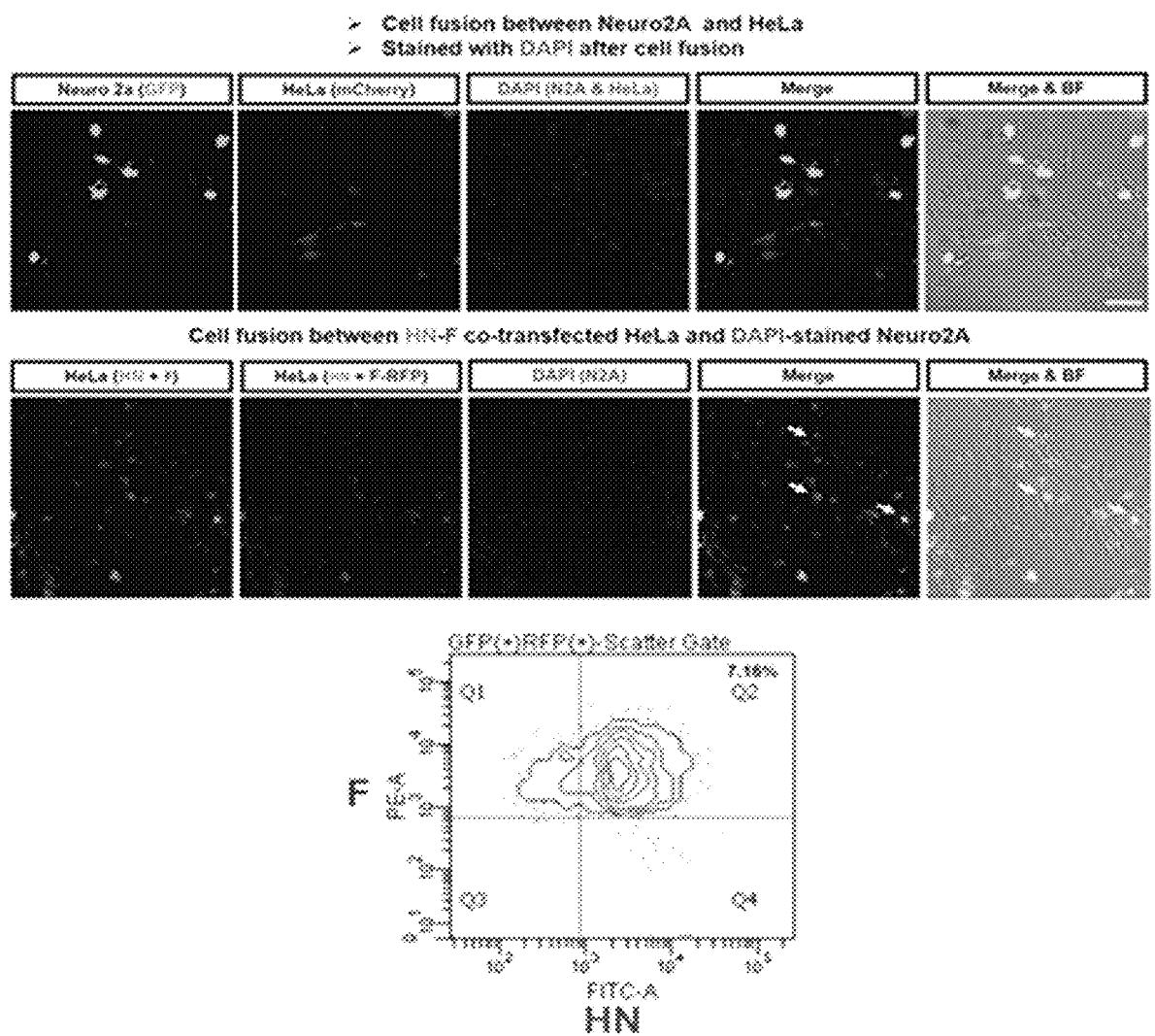
FIG. 13 illustrates an analysis of cell fusion ability with a N2A neuroblastoma cell line in HN/F-HeLa according to the exemplary embodiment of the present invention.

In order to evaluate the cell fusion ability of the HN/F-HeLa prepared above, the HN/F-HeLa and the N2A neuroblastoma cell line marked with the DAPI were subjected to cell fusion in the same manner as the method described in Example 4, and then the cells were collected, and the cell fusion rate of the HN/F-HeLa and the N2A neuroblastoma cell line was analyzed by a flow cytometry and a confocal laser microscope. As a control group, the N2A neuroblastoma cell line transduced with GFP and a HeLa cell line transduced with mCherry were subjected to cell fusion in the same manner as the method described in Example 4, and the cells were collected, and the cell fusion rate was compared and analyzed by a confocal laser microscope. As the analysis result, as shown in FIG. 13, it was confirmed that the cell fusion occurred in the HN/F-HeLa and the N2A neuroblastoma cell line and the cell fusion rate of the HN/F-HeLa and the N2A neuroblastoma cell line was increased by 7 times or more compared to the control group.

Such a result indicates that the cell fusion occurs by the HN and F proteins regardless of the cells.

Example 8. Analysis of Gene Expression Related with Cell Repair in Fused Cells of N2A Neuroblastoma Cell Line and HeLa Cell Line In order to confirm a cell damage repair mechanism during cell fusion by HN and F proteins, as shown in FIG. 14, it was confirmed that a binding motif of a TAR DNA-binding protein 43 (TDP-43) as a transcriptional factor (TF) was present in a promoter region of DDB1 by screening the promoter region of a gene DDB1 related with cell repair selected in Example 6.

In order to confirm that the expression of DDB1 increases by increasing TDP-43 during cell fusion by the HN and F proteins, as shown in FIG. 15, primers specifically binding to a mouse DDB1 (mDDB1) were prepared and total DNAs were extracted from the N2A neuroblastoma cell line and the HeLa cell line using the primers, and then the mouse-specific DDB1 gene was confirmed by PCR. In order to confirm that the expression of the DDB1 is regulated by the TDP-43, the TDP-43 was overexpressed in the N2A neuroblastoma cell line and then RNAs were extracted and analyzed using quantitative RT-PCR. Thereafter, the cell fusion was performed between the N2A neuroblastoma cell line and the HeLa cell line transduced with GFP and between the N2A neuroblastoma cell line and the HeLa cell line transduced with GFP-TDP-43 using a Sendai virus (HVJ) envelope cell fusion kit (GenomONE™-CF EX Sendai virus (HVJ) Envelope Cell Fusion Kit, COSMO BIO, Japan) according to the manufacturer's method, respectively, and then a ChIP chromatin immunoprecipitation (ChIP) assay (Millipore) was performed using a fusion GFP antibody (Rockland). As a result, as shown in FIG. 16, it was confirmed that mDDB1 was increased according to the fusion time in the fused cell line of the N2A neuroblastoma cell line and the HeLa cell line transduced with GFP-TDP-43, and the occupancy of TDP-43 in the mDDB1 promoter region was increased by 4 times or more, and the expression of DDB1 was regulated by increasing TDP-43.

Figure 17:
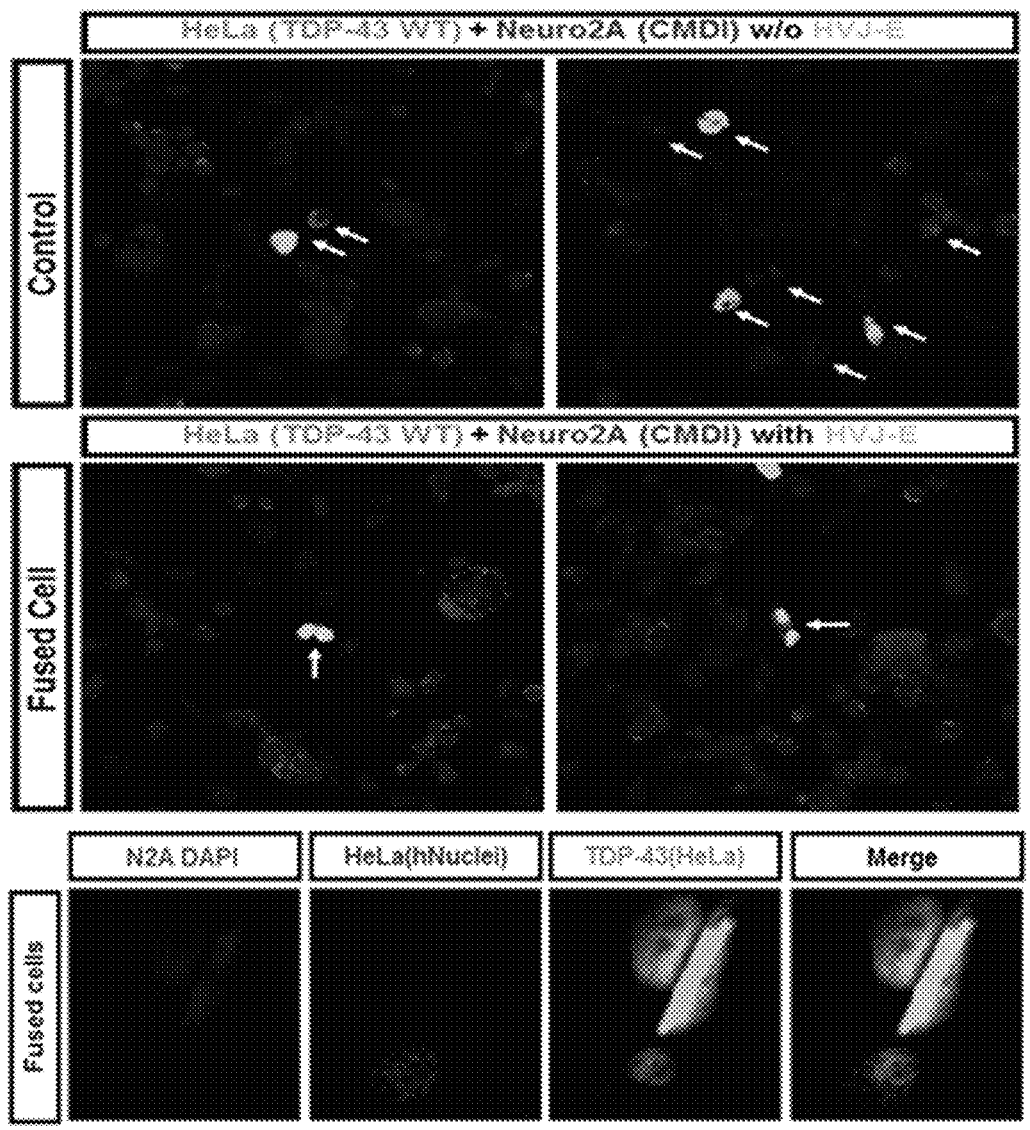
FIG. 17 illustrates an imaging analysis of translocation of TDP-43 from a nucleus of HeLa into a nucleus of the N2A neuroblastoma cell line in the fused cells of the HeLa cell line transduced with GFP-TDP-43 and the N2A neuroblastoma cell line according to the exemplary embodiment of the present invention.

Further, in order to confirm whether the TDP-43 is translocated into a nucleus of a recipient cell during cell fusion by the HN and F proteins, the N2A neuroblastoma cell line marked with CM-DiI and the HeLa cell line transduced with GFP-TDP-43 were cell-fused in the same manner as the method described above and then translocation of TDP-43 was analyzed by a confocal laser microscope after DAPI staining. In addition, the N2A neuroblastoma cell line was stained using NucBlue (ThermoFisher) and cell-fused with the HeLa cell line transduced with GFP-TDP-43 in the same manner as the method described above and then analyzed by a confocal laser microscope after performing immunostaining using a human nuclei antibody (abcam). As the analysis result, as shown in FIG. 17, it was confirmed that the TDP-43 in the HeLa cell line transduced with GFP-TDP-43 is translocated into the nucleus of the N2A neuroblastoma cell line.

Such a result indicates that an increase in expression of the gene DDB1 related with cell repair during the cell fusion by the HN and F proteins is regulated by binding to the promoter region of mDDB1 after TDP-43 of a donor cell is translocated into the nucleus of the recipient cell.

Figure 18:
FIG. 18 illustrates an intra-spinal cord injection method for injecting HN/F-hATMSCs in a cell damage-related mouse model (G93A SOD1 Tg mice) according to an exemplary embodiment of the present invention.
Figure 19:
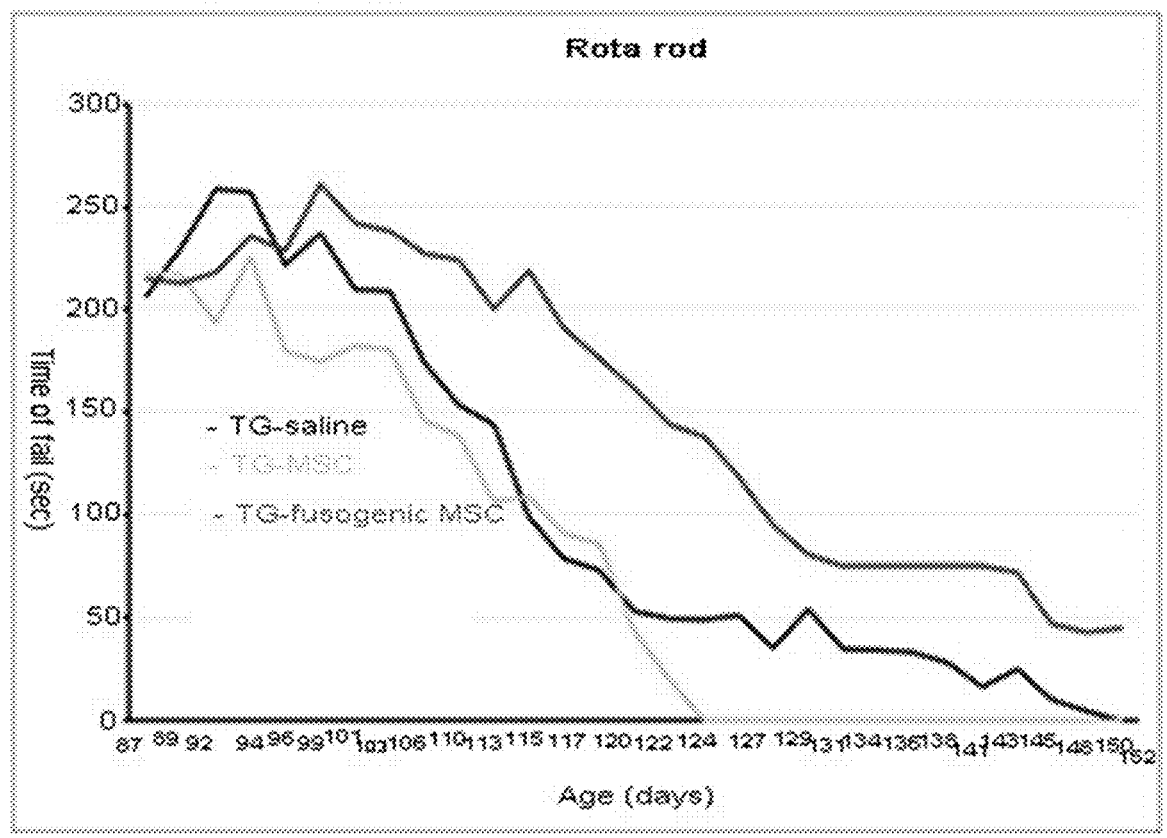
FIG. 19 illustrates an analysis of motion performance in a G93A SOD1 Tg mouse injected with HN/F-hATMSCs according to the exemplary embodiment of the present invention.

Example 9. Analysis of Therapeutic Effect Using HN/F-hATMSCs in Cell Damage-Related Disease Model In order to confirm the therapeutic effect using HN/F-hATMSCs in the cell damage-related disease, G93A SOD1 Tg mice (80 days after birth) as an amyotrophic lateral sclerosis (ALS) disease model were received from a Jackson laboratory. Thereafter, the G93A SOD1 Tg mice were divided into a control group (Tg-saline), a Tg-MSC group, and a Tg-fusogenic MSC group, and as shown in FIG. 18, a saline was injected in the control group, hATMSCs were injected in the Tg-MSC group, and the HN/F-hATMSCs prepared in Example 2 were injected in the Tg-fusogenic MSC group with the cell number of 0.5 to $2 \times 10^6$, respectively, and then a rota rod test was performed. As a result, as shown in FIG. 19, it was confirmed that in the Tg-fusogenic MSC group injected with the HN/F-hATMSCs, mobility was improved by the fusion of the HN/F-hATMSCs and the neuron cells by the HN/F proteins and the neuron cell damage repair.

Figure 21:
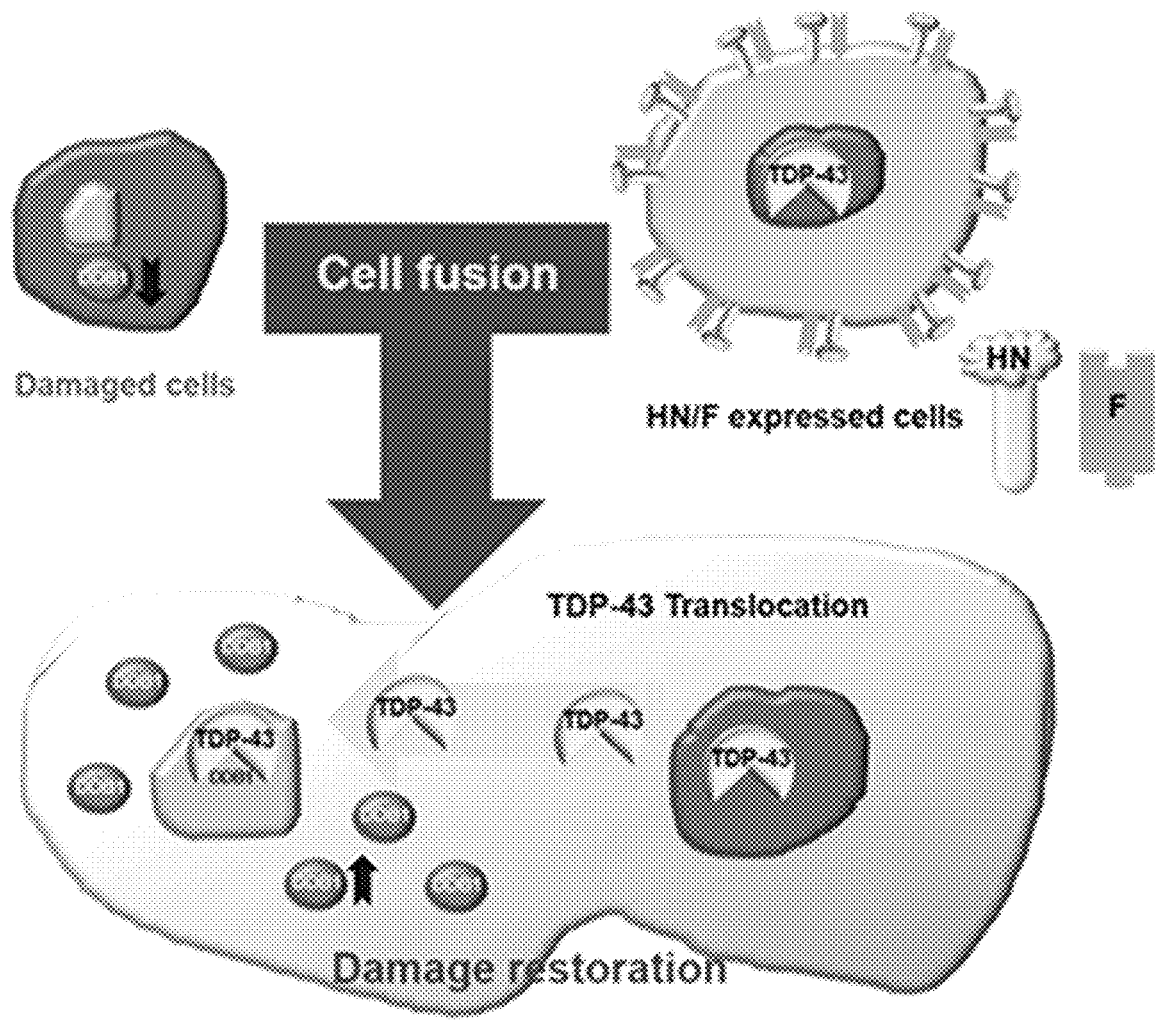
FIG. 21 is a schematic diagram illustrating a cell damage restoration mechanism by HN/F protein overexpressed cells in a cell damage-related disease.

These results indicate that as shown in FIG. 21, in the cell damage-related disease, the overexpressed cells of the HN/F proteins are fused with the damaged cells to translocate a transcription regulator in the overexpressed cells of the HN/F proteins into the nucleus of the damaged cells and regulate the expression of the gene involved in the cell repair in the damaged cells by the translocated transcription regulator, thereby restoring the damaged cells and treating the cell damage-related diseases.

Figure 20:
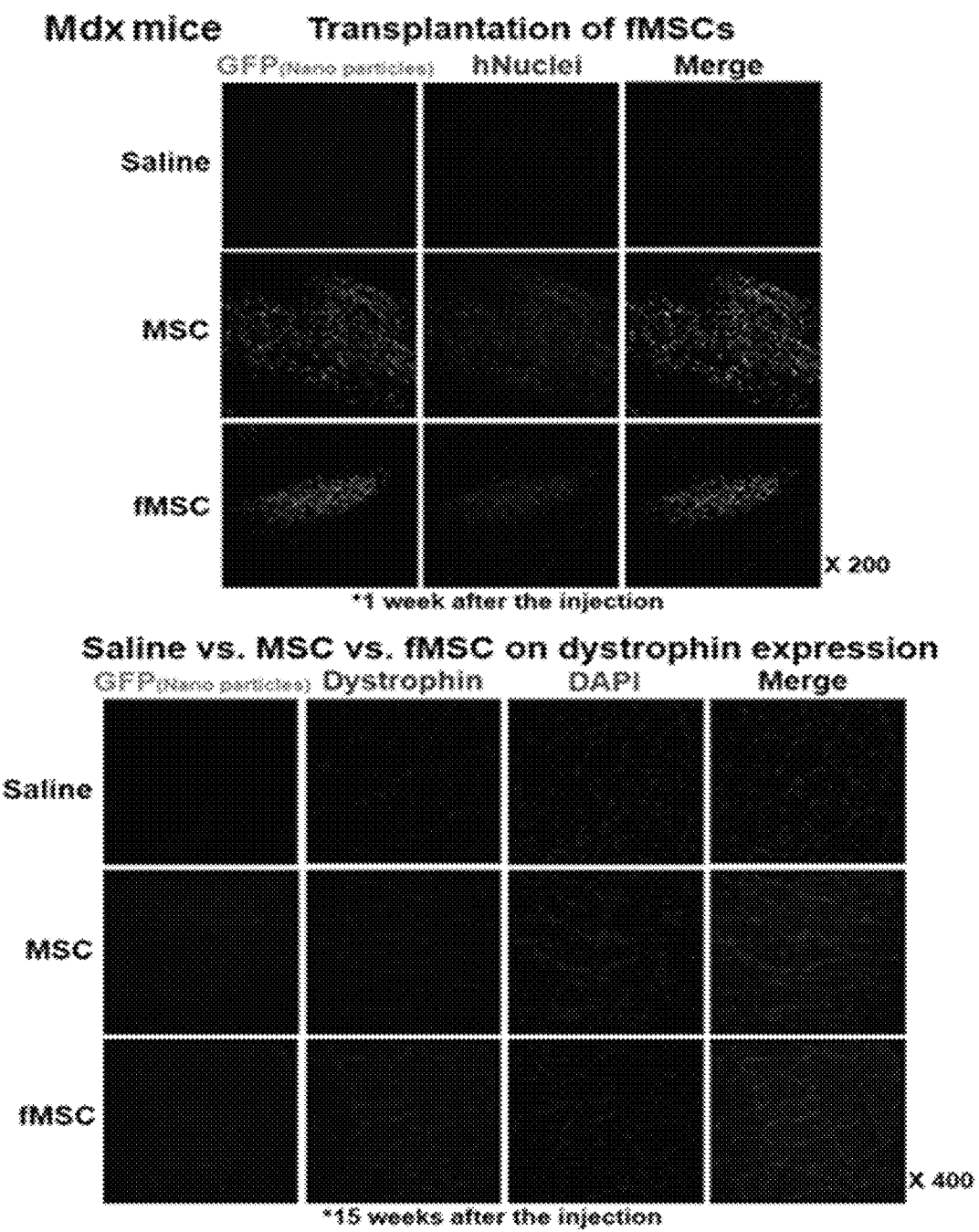
FIG. 20 illustrates survival rates and dystrophin expression of HN/F-hATMSCs in a skeletal muscle tissue of an mdx mouse injected with HN/F-hATMSCs according to the exemplary embodiment of the present invention.

Further, in order to confirm the therapeutic effect using the HN/F-hATMSCs in the damage-related diseases, mdx mice (2 to 4 weeks after birth) as a Duchenne muscular dystrophy (DMD) disease model were received from a Jackson laboratory. Thereafter, the mdx mice were divided into a control group (saline), a MSC group, and a fMSC group, and a saline was injected in the control group, hATMSCs marked with a green dye was injected in the MSC group, and HN/F-hATMSCs marked with a green dye was injected in the fMSC group with the cell number of 0.5 to $2\times10^6$ by using an intra-spinal cord injection, respectively, and skeletal muscles were isolated after 1 week. Survival rates of the hATMSCs and the fMSCs in the extracted skeletal muscles were analyzed by a confocal laser microscope using a green dye and a hNuclei antibody (abcam). Further, after 15 weeks of injection, the skeletal muscles were isolated and immunohistochemistry (IHC) was performed using a dystrophin antibody (abcam). As a result, as shown in FIG. 20, in the MSC group and the fMSC group, the survival rates of the hATMSCs and the HN/F-hATMSCs were confirmed by a green dye, respectively, and in the fMSC group, it was confirmed that the expression of a human normal dystrophin protein was significantly increased after 15 weeks of injection.

These results indicate that the human normal dystrophin protein may be expressed in the muscle of the fused mdx mice by the expression of the human normal dystrophyin gene by the cell fusion and thus, the cell fusion may be used as a delivery tool of gene therapy.

---

What is claimed is:

1. A method of fusing stem cells or progenitor cells to damaged nerve cells, comprising:
    administering stem cells or progenitor cells to the damaged nerve cells of a subject suffering from neurodegenerative diseases or neurological diseases,
    wherein the stem cells or progenitor cells are transformed with a vector including genes encoding hemagglutinin neuraminidase (HN) and fusion (F) proteins, and the stem cells or progenitor cells transformed with said vector express HN and F proteins and increase cell fusion with the damaged nerve cells compared to stem cells or progenitor cells not transformed with said vector.

2. The method of claim 1, wherein the HN and F proteins are derived from sendai virus, human immunodeficiency virus 1, influenza virus or vesicular stomatitis virus.

3. The method of claim 1, wherein the vector is any one selected from the group consisting of a linear DNA plasmid DNA, a non-viral recombinant vector, a viral recombinant vector, and an inducible gene expression vector system.

4. The method of claim 3, wherein the viral recombinant vector is any one selected from the group consisting of retroviruses, adenoviruses, adeno-associated viruses, helper-dependent adenoviruses, herpes simplex viruses, lentivirus vectors, and vaccinia viruses.

5. The method of claim 1, wherein the neurodegenerative diseases or the neurological diseases are selected from the group consisting of Alzheimer's disease (AD), dementia, multi-infarct dementia (MID), frontotemporal dementia, dementia with Lewy bodies, mild cognitive impairment, corticobasal degeneration, Parkinson's disease (PD), multiple system atrophy (MSA), Huntington's disease, spinal muscular atrophy, spinal bulbar muscular atrophy, progressive supranuclear palsy (PSP), metabolic brain disease, depression, epilepsy, dentatorubropallidoluysian atrophy (DRPLA), spinocerebellar ataxia, amyotrophic lateral sclerosis (ALS), multiple sclerosis, primary lateral sclerosis, progressive bulbar palsy, glaucoma, stroke, brain ischemia, post-encephalitic parkinsonism, Tourette's syndrome, restless legs syndrome, and attention deficit disorders with hyperactivity.

6. The method of claim 1, wherein the stem cells or progenitor cells are autologous, allogenic, or xenogenic cells.

7. The method of claim 1, wherein the stem cells are embryonic stem cells, adult stem cells, or induced pluripotent stem cells.

* * * * *

SEQUENCE LISTING

```
<160> NUMBER OF SEQ ID NOS: 13

<210> SEQ ID NO 1
<211> LENGTH: 72
<212> TYPE: DNA
<213> ORGANISM: Artificial Sequence
<220> FEATURE:
<223> OTHER INFORMATION: HN FP

<400> SEQUENCE: 1
aagcttatgg aacaaaaact catctcagaa gaggatctgg atggtgatag gggcaaacgt     60
gactcgtact gg                                                        72

<210> SEQ ID NO 2
<211> LENGTH: 39
<212> TYPE: DNA
<213> ORGANISM: Artificial Sequence
<220> FEATURE:
<223> OTHER INFORMATION: HN RP

<400> SEQUENCE: 2
gaattctcat cttttctcag ccattgcatc aaacccacc                            39

<210> SEQ ID NO 3
<211> LENGTH: 59
<212> TYPE: DNA
<213> ORGANISM: Artificial Sequence
<220> FEATURE:
<223> OTHER INFORMATION: F RP

<400> SEQUENCE: 3
aagcttatgc atcatcatca tcatcataca gcatatatcc agagatcaca gtgcatctc      59

<210> SEQ ID NO 4
<211> LENGTH: 39
<212> TYPE: DNA
<213> ORGANISM: Artificial Sequence
<220> FEATURE:
<223> OTHER INFORMATION: F RP

<400> SEQUENCE: 4
gaattctcat cttttctcag ccattgcatc aaacccacc                            39

<210> SEQ ID NO 5
<211> LENGTH: 19
<212> TYPE: DNA
<213> ORGANISM: Artificial Sequence
```

```
<220> FEATURE:
<223> OTHER INFORMATION: Partial HN FP

<400> SEQUENCE: 5
cgatctctgg atgtgttag                                              19

<210> SEQ ID NO 6
<211> LENGTH: 19
<212> TYPE: DNA
<213> ORGANISM: Artificial Sequence
<220> FEATURE:
<223> OTHER INFORMATION: Partial HN RP

<400> SEQUENCE: 6
ccacactagg gtataatgc                                              19

<210> SEQ ID NO 7
<211> LENGTH: 20
<212> TYPE: DNA
<213> ORGANISM: Artificial Sequence
<220> FEATURE:
<223> OTHER INFORMATION: Partial F FP

<400> SEQUENCE: 7
ctcatgataa ctgtggactc                                             20

<210> SEQ ID NO 8
<211> LENGTH: 20
<212> TYPE: DNA
<213> ORGANISM: Artificial Sequence
<220> FEATURE:
<223> OTHER INFORMATION: Partial F RP

<400> SEQUENCE: 8
ggttcagtag gctcttatac                                             20

<210> SEQ ID NO 9
<211> LENGTH: 20
<212> TYPE: DNA
<213> ORGANISM: Artificial Sequence
<220> FEATURE:
<223> OTHER INFORMATION: Human GAPDH  FP

<400> SEQUENCE: 9
agaaggctgg ggctcatttg                                             20

<210> SEQ ID NO 10
<211> LENGTH: 20
<212> TYPE: DNA
<213> ORGANISM: Artificial Sequence
<220> FEATURE:
<223> OTHER INFORMATION: Human GAPDH RP

<400> SEQUENCE: 10
aggggccatc cacagtcttc                                             20

<210> SEQ ID NO 11
<211> LENGTH: 1003
<212> TYPE: DNA
<213> ORGANISM: Artificial Sequence
<220> FEATURE:
<223> OTHER INFORMATION: TDP-43 binding motif

<400> SEQUENCE: 11
gagtcaagtc gagtgccagc tggggaggta caaatcatct tcagttccac ctggttcaaa    60
```

```
cctagctaca ctgatctctg cctcatttgt aaaatagggaa gttagctctc ctcctccggc    120
attctggaga tgcttcagga ctaggcttct gctgctcctc ctttggggtt ggggacatgg    180
aggctgtctg atgaagcctg ggacctgcat ctgcggggct gattgcacta gtcacctggg    240
tgtttaggct cttcctgtga aattcctgcg ttgtatttga gcttagaatt tgtatcgcag    300
tagaggcact aatagtgcta tcaagtaatt tagtggagag tcctttcgtt tctggagaaa    360
ttaaaagagg tgagcaaaca cacccccagg tgatgtgtga ggctgggatg attgttctaa    420
agtcagttga gggcattcga gggatcagga ggagctcgaa gaattaagca aaggaaagca    480
cgattctact ctgggatgtg cacagatggt cacctcttat ccccagtcta gtcctccgca    540
gcccttcctg ttttaaaaga gggaaaaccc cgaggacgcc tggagctatg gaggaaggaa    600
ggaggcagaa tctgaggaag gggcgcggat ctgggctggg aagccagcag gcggccactt    660
agggcgtagc agaccaaaga ggaggccagt tctgcctgcg taccggtact ctcgctctca    720
tccgggtact gcgacctctg gcggttagga gaaggcggga cctcaggggg cggggcctcg    780
cttggttggc cgcctcgggc tccgtaagtc ctccaagagg ccaggtgagg ccgtcccgtg    840
atcctctgcg cctggcctct ctggcctgca acgtgtctca ggggcggagg cagcagccac    900
ggagttggct gcgtgagggt ggggggttctc agtctcttcg ctcgcgcccg tctctctatc    960
gtcgctctag gcgccccacg ggccaaccca aggcctcaat atg                     1003

<210> SEQ ID NO 12
<211> LENGTH: 23
<212> TYPE: DNA
<213> ORGANISM: Artificial Sequence
<220> FEATURE:
<223> OTHER INFORMATION: DDB1 FP

<400> SEQUENCE: 12
atggaggctg tctgatgaag cct                                              23

<210> SEQ ID NO 13
<211> LENGTH: 23
<212> TYPE: DNA
<213> ORGANISM: Artificial Sequence
<220> FEATURE:
<223> OTHER INFORMATION: DDB1 RP

<400> SEQUENCE: 13
gctcctcctg atccctcgaa tgc                                              23
```